(12) United States Patent
Taylor et al.

(10) Patent No.: US 9,295,668 B2
(45) Date of Patent: Mar. 29, 2016

(54) USE OF AN AROMATASE INHIBITOR FOR THE TREATMENT OF HYPOGONADISM AND RELATED DISEASES

(75) Inventors: Ann Taylor, Wickford, RI (US); Lloyd B. Klickstein, Newton, MA (US)

(73) Assignee: Merco BioPharma 2 Limited, London (GB)

( * ) Notice: Subject to any disclaimer, the term of this patent is extended or adjusted under 35 U.S.C. 154(b) by 0 days.

(21) Appl. No.: 14/342,810

(22) PCT Filed: Sep. 6, 2012

(86) PCT No.: PCT/US2012/053844
§ 371 (c)(1),
(2), (4) Date: Mar. 5, 2014

(87) PCT Pub. No.: WO2013/036562
PCT Pub. Date: Mar. 14, 2013

(65) Prior Publication Data
US 2014/0309267 A1    Oct. 16, 2014

Related U.S. Application Data

(60) Provisional application No. 61/532,459, filed on Sep. 8, 2011, provisional application No. 61/638,588, filed on Apr. 26, 2012.

(51) Int. Cl.
*A61K 31/4196* (2006.01)
*A61K 9/48* (2006.01)

(52) U.S. Cl.
CPC ............. *A61K 31/4196* (2013.01); *A61K 9/485* (2013.01); *A61K 9/4833* (2013.01); *A61K 9/4858* (2013.01); *A61K 9/4866* (2013.01)

(58) Field of Classification Search
CPC .................................................. A61K 31/4196
See application file for complete search history.

(56) References Cited

U.S. PATENT DOCUMENTS 5,637,605 A    6/1997    Stanek

FOREIGN PATENT DOCUMENTS

| EP | 0490816 A2 | 6/1992 |
| WO | 02/083240 | 10/2002 |
| WO | 03/082254 A1 | 9/2003 |

OTHER PUBLICATIONS

Leder et al. Journal of Clinical Endocrinology and Metabolism, 2004, vol. 89, pp. 1174-1180.*
Shetty, G et al: "Effect of estrogen deprivation on the reproductive physiology of male and female primates", Journal of Steroid Biochemistry and Molecular Biology. vol. 61, No. 3-6, pp. 157-166, 1997.
Shetty, G et al: "Effect of long-term treatment with aromatase inhibitor on testicular function of adult male bonnet monkeys (*M. radiate*)—Comparative study among different species of mammals", Steroids, vol. 63, No. 7-8, pp. 414-420, 1998.
De Boer, H et al: "Letrozole normalizes serum testosterone in severely obese men with hypogonadotropic hypogonadism", Diabetes, Obesity and Metabolism, vol. 7, No. 3 pp. 211-215, 2005.
Lang, M et al: "Structure-activity relationships and binding model of novel aromatase inhibitorS", Journal of Steroid Biochemistry and Molecular Biology, vol. 44, No. 4-6, pp. 421-428, 1993.
Loves, Sandra, et.al: "Letrozole once a week normalizes serum testosterone in obesity-related male hypogonadism", European Journal of Endocrinology, (2008) vol. 158, pp. 741-747.
Edelstein, Daniel et.al.: The latest options and future agents for treating male hypogonadism, Expert Opinion, vol. 8 (17), pp. 2991-3008 (2007).
Batzl-Hartmann, Ch. Et.al: "Pharmacological profile of CGP47645, a new non-steroidal aromatase inhibitor with a long duration of action", XVI International Cancer Congress in India 1994 New Delhi, India Oct. 30-Nov. 5, 1994, Copyright: Monduzzi Editorea S.p. A. Bologna Italy, pp. 3041-3047, 1994.
Zumoff, Barnett et.al.: "Reversal of the hypogonadotropic hypogonadism of obese men by administration of the aromatase inhibitor testolactone", Metabolism, vol. 52(9), Sep. 2003, pp. 1126-1128.
De Ronde, Willem et.al.: "Aromatase inhibitors in men: effects and therapeutic options", Reproductive Biology and Endocronolgy 2011 vol. 9(93), pp. 1-7.
Leder, Benjamin et.al.: "Effect of aromatase inhibition on bone metabolism in elderly hypogonadal men", Osteoporosis Intl. (2005) 16:1487-1494.
Burnett-Bowie, Sherri-Ann et.al.: "Effects of aromatase inhibition on bone mineral density and bone turnover in older men with low testosterone levels", Journal of Clin Endocrinol Metab., Dec. 2009, 94(12): 4785-4792.

* cited by examiner

*Primary Examiner* — James D Anderson
(74) *Attorney, Agent, or Firm* — Wolff IP, a Prof. Corp.; Jessica R. Wolff, Esq.

(57) ABSTRACT

The aromatase inhibitor 4,4'-[fluoro-(1-H-1,2,4-triazol-1-yl)methylene]bisbenzonitrile increases testosterone levels and treats hypogonadism and related diseases. A particular dosing regimen is disclosed as well as pharmaceutical compositions comprising said of 4,4'-[fluoro-(1-H-1,2,4-triazol-1-yl)methylene]bisbenzonitrile, optionally in combination with other active ingredients and kits comprising the pharmaceutical compositions.

21 Claims, No Drawings

USE OF AN AROMATASE INHIBITOR FOR THE TREATMENT OF HYPOGONADISM AND RELATED DISEASES

FIELD OF THE INVENTION

This invention relates to a method of increasing testosterone levels and treating hypogonadism and related diseases with the aromatase inhibitor 4,4'-[fluoro-(1-H-1,2,4-triazol-1-yl)methylene]-bisbenzonitrile. The present invention further relates to a method of increasing testosterone levels and treating hypogonadism and related diseases with the aromatase inhibitor 4,4'-[fluoro-(1-H-1,2,4-triazol-1-yl)methylene]-bisbenzonitrile in a particular dosing regimen. The invention also relates to pharmaceutical compositions comprising said aromatase inhibitor 4,4'-[fluoro-(1-H-1,2,4-triazol-1-yl)methylene]-bisbenzonitrile, optionally in combination with other active ingredients. Furthermore, the present invention relates to kits comprising said pharmaceutical compositions together with instructions how to administer them.

BACKGROUND OF THE INVENTION

The enzyme aromatase (CYP 19) is highly expressed in adipose tissue, where it converts testosterone to estradiol. In human overweight or obesity, excess adipose tissue is associated with excess aromatase activity, which in turn results in higher levels of estradiol in both men and women. In overweight and obese men, the relative excess of estradiol can feed back to the hypothalamic pituitary axis, suppressing gonadotropin secretion and thereby suppressing testicular testosterone production as well as spermatogenesis. Thus, severe obesity is associated with relative androgen deficiency in men. This condition can be called OHH or obese hypogonadotropic hypogonadism or hypogonadotropic hypogonadism in obese men.

In the 1999-2002 National Health and Nutrition Examination Survey data set, 27.5% of men over the age of 20 in the United States had a Body Mass Index (BMI) above 30 kg/m$^2$. The prevalence of obesity is expected to continue to increase in the United States, and in both developed and developing countries around the world. In one study of 160 men referred for medical or surgical treatment of obesity, hypogonadotropic hypogonadism was present in 36% overall. In this study, the prevalence of hypogonadotropic hypogonadism rose linearly from 7.4% in those with a BMI of 30-35 kg/m$^2$ to 59.2% in those with a BMI above 50 kg/m$^2$ [Hofstra, et al 2008]. Based on the prevalence of obesity, we estimate that up to 1.5 million men in the US and 1 million men in Europe would have androgen deficiency due to hypogonadotropic hypogonadism.

The consequences of testosterone deficiency are many, including symptoms of decreased libido, decreased spontaneous erections, decreased fertility, loss of body hair and reduced shaving, low bone mineral density, increased risk of fractures, decreased muscle mass and strength and fatigue [Bhasin, et al 2006]. In addition, more recent studies have demonstrated that testosterone deficiency in older men and in men with obesity is also associated with metabolic abnormalities including insulin resistance, glucose intolerance, and lipid abnormalities, contributing to an increased incidence of metabolic syndrome, and likely increased risk of cardiovascular disease. In one study, up to 15% of diabetic men had clear hypogonadism (testosterone <300 ng/dL or <8 nmol/L) and up to 50% had testosterone in the lower range of normal (<12 nmol/L or <450 ng/dL) [Kapoor, et al 2006 and 2007]. An association has been established between low testosterone levels and various cardiovascular risk factors. Recent epidemiological studies have also linked low testosterone with cardiovascular mortality [Maggio et al. 2009].

Guidelines for the treatment of male hypogonadism have been developed by several organizations, including the Endocrine Society of the United States stating that "We recommend testosterone therapy for symptomatic men with androgen deficiency, who have low testosterone levels, to induce and maintain secondary sex characteristics and to improve their sexual function, sense of well-being, muscle mass and strength, and bone mineral density" [Bhasin, et al 2006]. Replacement of testosterone is typically recommended by either intramuscular or transdermal routes as the standard of care for men with documented hypogonadism (testosterone <300 ng/dL associated with symptoms of low testosterone) and can normalize libido, muscle mass and strength [Bhasin, et al 2006]. In addition, testosterone replacement improves insulin resistance in men with hypogonadism [Naharci, et al 2007].

Next to overweight and obesity and its associated excess aromatase activity, other causes of hypogonadism in men include primary testicular failure, which may be due to endogenous defects or acquired due to trauma, infection, or chemo- or radiation therapy, and secondary failures with suppression of gonadotropins that may be due to stress, concomitant diseases, or hypothalamic pituitary disorders.

Current therapies for testosterone deficiency are limited. Most hypogonadal men are treated with intramuscular injections of testosterone every 2 to 4 weeks, typically requiring a visit to a health care provider. Some men choose testosterone gels or patches that are usually applied daily. Men with OHH desiring fertility may be treated with intramuscular or subcutaneous injections of HCG or gonadotropins. There are various complications of testosterone replacement which may include gynecomastia due to the excessive conversion of exogenous testosterone to estradiol, infertility due to suppression of gonadotropins, mood swings due to the rise and fall of testosterone after intramuscular injections, and injection site or application site irritation. Excess testosterone can lead to polycythemia (erythrocytosis), prostate enlargement, sleep apnea, and worsening heart failure, in addition to aggressiveness. The Endocrine Society recommends "against starting testosterone therapy in patients with breast or prostate cancer, a palpable prostate nodule or induration or prostate-specific antigen greater than 3 ng/ml without further urological evaluation, erythrocytosis (hematocrit >50%), hyperviscosity, untreated obstructive sleep apnea, severe lower urinary tract symptoms with International Prostate Symptom Score (IPSS) [Barry, et al 1992] greater than 19, or class III or IV heart failure.", and that "men receiving testosterone therapy should be monitored using a standardized plan" [Bhasin, et al 2006].

Oral androgen therapies are generally contraindicated because of first pass hepatic effects that dramatically suppress HDL, increase thrombogenic factors, and often cause liver function abnormalities. These hepatic effects of androgens have also so far limited the clinical utility of selective androgen receptor modulators (SARMs).

Some commercially available aromatase inhibitors have also been tested for efficacy in hypogonadal men in a few, small proof of concept studies. Letrozole, given at doses of 2.5 mg weekly, increased total testosterone into the normal range, suppressed total estradiol, and increased LH and FSH in 12 OHH men [de Boer, et al 2005, Loves, et al 2008]. At this fixed dosing interval, free testosterone rose above the normal range in approximately half of the subjects. Other investigators have assessed the effects of aromatase inhibitors (letrozole [de Boer, et al 2005, Lapauw, et al 2009, Loves, et al 2008] CGS 20267 [Trunet, et al 1993] and anastrozole [Medras, et al 2007]) in uncontrolled studies.

One potential draw-back of all clinical studies conducted so far is that the aromatase inhibitors used in studies—anastrozole and letrozole—were developed for the treatment of hormone dependent cancers such as breast cancer in postmenopausal women and might therefore not be optimally suitable to treat hypogonadism in male patients, in particular in view of the optimal dosages and dosing regimen, and the potential side effects. Dosages and dosing regimens assessed so far in the clinical trials comprised the weekly administration of 2.5 mg or 1 mg of the respective aromatase inhibitor for the treatment of hypogonadism—which corresponds to the dosages used for adjuvant treatment of postmenopausal women with hormone receptor positive early breast cancer, but not an optimized treatment regimen for hypogonadism.

Indeed, human PK/PD studies of marketed aromatase inhibitors in men with hypogonadism have shown that e.g. letrozole at a 2.5 mg weekly dose resulted in excessive free testosterone levels in approximately half the subjects [Loves, et al, 2008]. There have been no studies so far to fully assess the effects of aromatase inhibitors on testosterone levels and how to actually achieve normalization of testosterone levels in men with hypogonadism.

Thus, optimized treatment regimens providing the relief of the testosterone deficiency driven symptoms of hypogonadism with minimal side effects are required. The development of an aromatase inhibitor especially suited for male patients with decreased testosterone levels would provide a novel treatment option for this so far insufficiently targeted disease.

In addition to the clinically approved non-steroidal aromatase Inhibitors anastrozole, letrozole and fadrozole, which are approved for the treatment of hormone dependent breast cancer by daily administration of dosages in the mg range, several other aromatase inhibitors have been described in the patent and scientific literature. One of these compounds is the aromatase inhibitor 4,4'-[fluoro-(1-H-1,2,4-triazol-1-yl)methylene]bisbenzonitrile, also known as 4-[α-4-Cyanophenyl)-α-fluoro-1-(1,2,4-triazolyl)methyl]-benzonitrile or CGP47645, first described in 1992 [EP 490 816 and U.S. Pat. No. 5,637,605], having the following structural formula

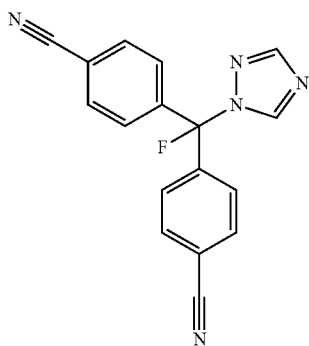 [SMILES: N#Cc1ccc(C(F)(c2ccc(C#N)cc2)n2cncn2)cc1]

CGP47645 is a fluoro-derivative of letrozole with a prolonged duration of action. Preliminary in-vitro and in-vivo experiments with this compound in rats and monkeys showed a similar up to 10 fold higher potency of aromatase inhibition as letrozole, and demonstrated the potential for less than daily treatment regimen. A once weekly administration of 3 mg/kg of CGP47645 was considered as an effective dose achieving medical castration in adult female rats [Batzl-Hartmann et al, 1994]. It was concluded that the half-life of CGP47645 is long enough to maintain endocrine efficacy similar to that of ovariectomy with a once-weekly dosing schedule [Bhatnagar et al, 1996]. However, no further studies of this drug compound have been carried out and its potential for the treatment of hormone dependent cancers or other diseases such as endometriosis was never investigated.

Currently, there are no oral pharmacological treatment regimens approved to treat hypogonadism and/or testosterone deficiency in obese male patients in the US and most other countries. As set out above, currently, testosterone, HCG or gonadotropin injections are so far the only option for these patients. Therefore, there is an important unmet medical need in this population for the development of a pharmacological treatment that reduces the disorders and symptoms associated with testosterone deficiency.

In particular, an oral therapy that normalizes systemic testosterone, but does not significantly increase local hepatic exposure to androgens would be highly desirable. In addition, it would be desirable to have a treatment regimen available achieving a more physiologic testosterone replacement.

In consideration of all problems and disadvantages connected with the so far known treatment options for male hypogonadism and testosterone deficiency, in particular hypogonadotropic hypogonadism in obese or overweight men, it would be highly advantageous to provide a new treatment option overcoming the aforementioned drawbacks and indeed providing relief or at least improvement for these patients.

SUMMARY OF THE INVENTION

Accordingly, in a first aspect the present invention relates to the compound 4,4'-[fluoro-(1-H-1,2,4-triazol-1-yl)methylene]bisbenzonitrile for use in the treatment of a male patient in need of increased testosterone levels.

In one embodiment said male patient is overweight or obese.

In a second aspect the present invention relates to the compound 4,4'-[fluoro-(1-H-1,2,4-triazol-1-yl)methylene] bisbenzonitrile for use in the treatment of hypogonadism in a male patient.

In a third aspect, the present invention relates to the compound 4,4'-[fluoro-(1-H-1,2,4-triazol-1-yl)methylene]bisbenzonitrile for use in the treatment of hypogonadism in an overweight or obese male patient.

In a fourth aspect, the present invention relates to the compound 4,4'-[fluoro-(1-H-1,2,4-triazol-1-yl)methylene]bisbenzonitrile for use in the treatment of hypogonadotropic hypogonadism in a male patient.

In a further aspect, the present invention relates to the compound 4,4'-[fluoro-(1-H-1,2,4-triazol-1-yl)methylene] bisbenzonitrile for use in the treatment of hypogonadotropic hypogonadism in an overweight or obese male patient.

In a further aspect, the present invention relates to the compound 4,4'-[fluoro-(1-H-1,2,4-triazol-1-yl)methylene] bisbenzonitrile for increasing, preferably normalizing testosterone levels in a male patient with hypogonadism or hypogonadotropic hypogonadism, preferably in an overweight or obese male patient with hypogonadism or hypogonadotropic hypogonadism.

In a further aspect, the present invention relates to the compound 4,4'-[fluoro-(1-H-1,2,4-triazol-1-yl)methylene] bisbenzonitrile for use in the treatment of a male patient in need of increased testosterone levels, wherein the compound is provided in a form comprising from about 0.0005 mg to about 5.0 mg, preferably from about 0.0005 mg to about 2.0 mg 4,4'-[fluoro-(1-H-1,2,4-triazol-1-yl)methylene]bisbenzonitrile per dose and is for administration according to a dosing regimen having a dosing periodicity ranging from about once daily to about once every 60 days.

In a further aspect the present invention relates to the use of 4,4'-[fluoro-(1-H-1,2,4-triazol-1-yl)methylene]bisbenzonitrile for the manufacture of a medicament for the treatment of a male patient in need of increased testosterone levels.

In a further aspect the present invention relates to the use of 4,4'-[fluoro-(1-H-1,2,4-triazol-1-yl)methylene]bisbenzonitrile for the manufacture of a medicament for the increasing, preferably normalizing testosterone levels in an overweight or obese male patient with hypogonadotropic hypogonadism.

A further aspect of the present invention relates to the use of 4,4'-[fluoro-(1-H-1,2,4-triazol-1-yl)methylene]bisbenzonitrile for the manufacture of a medicament for the treatment of a male patient in need of increased testosterone levels, wherein the compound is provided in a form comprising from about 0.0005 mg to about 5.0 mg, preferably from about 0.0005 mg to about 2.0 mg 4,4'-[fluoro-(1-H-1,2,4-triazol-1-yl)methylene]bisbenzonitrile per dose and is for administration according to a dosing regimen having a dosing periodicity ranging from about once daily to about once every 60 days.

In a further aspect the present invention relates to an oral pharmaceutical composition comprising from about 0.0005 mg to about 5.0 mg, preferably from about 0.0005 mg to about 2.0 mg 4,4'-[fluoro-(1-H-1,2,4-triazol-1-yl)methylene]bisbenzonitrile per dose, optionally in combination with one or more pharmaceutically acceptable excipients.

According to a further aspect of the invention there is provided a kit of parts comprising (i) such a pharmaceutical composition comprising 4,4'-[fluoro-(1-H-1,2,4-triazol-1-yl)methylene]bisbenzonitrile, optionally in combination with one or more pharmaceutically acceptable excipients; together with (ii) instructions how to administer said pharmaceutical composition for the treatment of a male patient in need of increased testosterone levels, in particular for the treatment of hypogonadism in a male patient, preferably an overweight or obese male patient.

In a further aspect the present invention relates to a method for the treatment of a male patient in need of increased testosterone levels comprising administering to said patient an effective amount of 4,4'-[fluoro-(1-H-1,2,4-triazol-1-yl)methylene]bisbenzonitrile.

According to a further aspect of the invention there is provided a method for the treatment of hypogonadism comprising the administration to a male patient in need thereof an effective amount of 4,4'-[fluoro-(1-H-1,2,4-triazol-1-yl)methylene]bisbenzonitrile.

The dose can be from about 0.0005 mg to about 5.0 mg, preferably from about 0.0005 mg to about 2.0 mg and administered in a dosing regimen having a dosing periodicity ranging from about once daily to about once every 60 days.

ABBREVIATIONS

Throughout this specification, the following abbreviations will be used:
AE adverse event
ANCOVA analysis of covariance model
AUC area under the concentration time curve
BA bioavailability
BE bioequivalence
BMD Bone Mineral Density
BMI Body Mass Index
EOS end of study
FDA Food and Drug Administration
GCP good clinical practice
GnRH gonadotrophic hormone releasing hormone
HOMA-IR homeostatic model assessment of insulin resistance
HRQoL Health-related Quality of Life
i.v. intravenous(ly)
LH luteinizing hormone
LLN Lower Limit of the Norm
LLOQ lower limit of quantification
mL millilitre(s)
mm Hg millimeters of mercury
NCS not clinically significant
NOAEL no-observable adverse effect level
NTEL no-toxic-effect level
o.d. or q.d. once a day
p.o. per os/by mouth/orally
PD pharmacodynamics
pH negative log hydrogen ion concentration
PK pharmacokinetics
SAE serious adverse event
SOP Standard Operating Procedure
TBD to be determined
ULN Upper Limit of the Norm

DEFINITIONS

Throughout this specification and in the claims that follow, the following terms are defined with the following meanings, unless explicitly stated otherwise.

As used herein, the terms "comprising" and "including" are used herein in their open, non-limiting sense.

Where the plural form is used for compounds, salts, and the like, this is taken to mean also a single compound, salt, or the like.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The term "aromatase inhibitor" is defined as a compound that prevents the formation of estrogens from their metabolic precursors by inhibiting the enzyme aromatase.

As used herein, the term "compound" refers to 4,4'-[fluoro-(1-H-1,2,4-triazol-1-yl)methylene]bisbenzonitrile, also known as 4-[α-4-Cyanophenyl)-α-fluoro-1-(1,2,4-triazolyl)-methyl]-benzonitrile or CGP47645, first described in 1992 within EP 490 816 and U.S. Pat. No. 5,637,605, the disclosure of which is hereby incorporated by reference herein.

The compound 4,4'-[fluoro-(1-H-1,2,4-triazol-1-yl)methylene]bisbenzonitrile is a crystalline compound with a sharp melting endotherm at 169.5° C. The crystalline powder is not hygroscopic and is poorly soluble in water.

4,4'-[fluoro-(1-H-1,2,4-triazol-1-yl)methylene]bisbenzonitrile (CGP47645) is a highly specific and potent aromatase inhibitor which was shown here within to have a longer half life in humans than does letrozole (Femara®), a marketed aromatase inhibitor to which CGP47645 is structurally related. In vitro experiments with human placental microsomal aromatase demonstrated an $IC_{50}$=6 nM. Oral administration of CGP47645 to rats demonstrated a T½ of 75 hours. The exposure expressed as AUC was proportional to the administered dose. In two different aromatase dependent experimental models, inhibition of androstenedione-induced uterine hypertrophy in rats and inhibition of DMBA-induced mammary tumors in rats, the $ED_{50}$ was 0.003 mg/kg and 0.01 mg/kg, respectively. These results suggested CGP47645 is approximately 10-fold more potent than letrozole as an aromatase inhibitor.

The term "compound" shall here be understood to cover any and all isomers (e.g., enantiomers, stereoisomers, diastereomers, rotomers, tautomers) or any mixture of isomers, prodrugs, and any pharmaceutically acceptable addition salts of said compound, unless stated otherwise.

The term "testosterone level" in the context of the present invention refers to either total testosterone or free testosterone levels measured in blood serum. In one embodiment, the term "testosterone level" refers to blood serum total testosterone. "Total testosterone" includes testosterone that is bound to sex hormone-binding globulin (SHBG) and is therefore not bioavailable and testosterone which either is free or loosely bound to other proteins (non-SHBG-bound). Free or bioavailable testosterone levels will be calculated from the total testosterone and SHBG levels. Preferably testosterone levels are determined in the morning, between 6 am and 12 pm, as "morning testosterone levels". Testosterone and SHBG levels can be determined using a simple blood tests performed by a laboratory.

The term "a male patient in need of increased testosterone levels" is defined as a male individual having serum total testosterone levels below 450 ng/dL or below 12 nmol/L. In one embodiment the term "a male patient in need of increased testosterone levels" is defined as a male individual having serum total testosterone levels below 400 ng/dL, or below 350 ng/dL, or below 10 nmol/L. In one embodiment the term "a male patient in need of increased testosterone levels" is defined as a male individual having serum total testosterone levels below 300 ng/dL or below 8 nmol/L.

In another embodiment, the term "a male patient in need of increased testosterone levels" is defined as a male individual having—irrespective of testosterone levels—elevated serum total estradiol levels (and/or elevated total serum estrone and/or estrone sulfate and/or estriol levels). Elevated estradiol levels within the context of the present invention are defined as estradiol levels being above the ULN of the respective approved assay.

The term "overweight patient" as defined herein refers to a patient with a Body Mass Index (BMI) of equal or greater than 25 kg/m² and less than 30 kg/m², calculated from their body weight and body height.

The term "obese patient" as defined herein refers to a patient with a Body Mass Index (BMI) of equal or greater than 30 kg/m², calculated from their body weight and body height.

The Body mass index (BMI), a measurement which compares weight and height, defines people as overweight (pre-obese) when their BMI is between 25 kg/m² and 30 kg/m², and obese when it is greater than 30 kg/m².

As used herein, the term "hypogonadism" is used to refer to subjects having a total testosterone level of less than 400 ng/dL, in certain embodiments of less than 350 ng/dL, and in further embodiments of less than 300 ng/dL. Alternatively, the term "hypogonadism" is used to refer to subjects having a total testosterone level of less than 12 nmol/L, in certain embodiments of less than 10 nmol/L, and in further embodiments of less than 8 nmol/L. In one embodiment, the term "hypogonadism" is used to refer to a male individual having morning serum total testosterone levels below 300 ng/dL or below 8 nmol/L.

The term "hypogonadotropic patient" as defined herein refers to a patient with inappropriately low gonadotropins. In particular, a patient with "inappropriately low gonadotropins" is defined as a patient with (i) luteinizing hormone (LH) levels ≤ULN of the respective approved assay, (ii) follicle stimulating hormone (FSH) levels ≤ULN, and (iii) estradiol within or above the normal range (defined as ≥LLN of the approved assay).

In another embodiment, the "hypogonadotropic patient" shall have "inappropriately low gonadotropins" as defined above, and normal hypothalamic/pituitary function including (i) prolactin levels within the normal range, (ii) thyroid stimulating hormone (TSH) levels within the normal range, and (iii) ferritin levels within the normal range.

The term "hypogonadotropic hypogonadism" or "a patient with hypogonadotropic hypogonadism" as defined herein refers to a male subject suffering from hypogonadism as defined herein, and being hypogonadotropic as defined herein.

The term "obese, hypogonadotropic hypogonadism" or "an obese, hypogonadotropic male patient with hypogonadism" or "hypogonadotropic hypogonadism in obese men" as defined herein refers to a male subject being obese as defined herein, suffering from hypogonadism as defined herein, and being hypogonadotropic as defined herein. In one embodiment, such patient is defined as a subject meeting the following criteria: (a) having a Body Mass Index (BMI) ≥30 kg/m², (b) having a morning serum total testosterone level below 400 ng/dL, preferably below 350 ng/dL, and more preferably of below 300 ng/dL, and (c) having inappropriately low gonadotropins as defined herein above, and (d) having normal hypothalamic/pituitary function, as defined herein above.

The term "overweight hypogonadotropic hypogonadism" or "an overweight, hypogonadotropic male patient with hypogonadism" or "hypogonadotropic hypogonadism in overweight men" as defined herein refers to a male subject being overweight as defined herein, suffering from hypogonadism as defined herein, and being hypogonadotropic as defined herein. In one embodiment, such patient is defined as a subject meeting the following criteria: (a) having a Body Mass Index (BMI) of equal or greater than 25 kg/m² and less than 30 kg/m², (b) having a morning serum total testosterone level below 400 ng/dL, preferably below 350 ng/dL, and more preferably of below 300 ng/dL, and (c) having inappropriately low gonadotropins, as defined herein above, and (d) having normal hypothalamic/pituitary function, as defined herein above.

As used herein, the term "normalization of testosterone levels" is defined as an elevation of the serum total testosterone levels, preferably the morning serum total testosterone levels, to above 300 ng/dL or above 8 nmol/L. In one embodiment, it is defined as an elevation of the serum total testosterone levels, preferably the morning serum total testosterone levels, to above 350 ng/dL, to above 400 ng/dL, to above 450 ng/dL or to above 8 nmol/L.

As used herein, the term "increasing testosterone levels" is defined as increasing the total morning serum testosterone level after administration of the compound according to the invention by at least 10% in comparison to the testosterone level prior to administration of the compound. In certain embodiments, the term "increasing testosterone levels" is defined as increasing the total morning serum testosterone level after the administration of a therapeutically effective amount of the compound to a male patient according to the invention by at least 15%, at least 20%, at least 25%, at least 30%, at least 35%, at least 40%, at least 45%, at least 50%, at least 55%, at least 60%, at least 65%, at least 70%, or even higher, in comparison to the testosterone level prior to administration of the compound.

The term "treatment of hypogonadism" as defined herein refers to the treatment of the disease hypogonadism, wherein the disease is defined as set out in the introductory part here within. In one aspect, the term "treatment of hypogonadism" comprises the treatment of patients with reduced serum testosterone levels.

As used herein, the term "a dosing regimen having a dosing periodicity ranging from about once daily to about once every 60 days" refers to a dosing regimen wherein the active compound could be administered once every 1, 2, 3, 4, 5, 6, 7, 8, 9, 10, 11, 12, 13, 14, . . . 21, . . . , 26, 27, 28, 29, 30 . . . , 35, . . . , 42, . . . , 49, . . . , 56, 57, 58, 59, 60 days. This term comprises e.g. dosing regimens having (i) a dosing periodicity ranging from about once daily to about once every 60 days, (ii) a dosing periodicity ranging from about once every 2 days to about once every 40 days or 6 weeks, (iii) a dosing periodicity ranging from about once every 5 days to about once monthly or about once every 4 weeks or about once every 30 days, (iv) a dosing periodicity ranging from about once weekly or about once every 7 days to about once every 3 weeks or about once every 20 days, or (v) a dosing periodicity ranging from about once weekly or about once every 7 days to about once biweekly or once every 10 days.

In this context the term "about" shall have the meaning from "plus/minus 1 day" for a dosing regimen of once every 3 days to "plus/minus 10 days" for a dosing regimen of once every 60 days. A dosing regimen of "about once every 3 days" refers to a dosing regimen of one dose administered every 3 days plus/minus 1 day; a dosing regimen of "about once weekly" refers to a dosing regimen of one dose administered every 7 day plus/minus 2 days; a dosing regimen of "about once biweekly" refers to a dosing regimen of one dose administered every 14 day plus/minus 3 days; a dosing regimen of "about once every 4 weeks" refers to a dosing regimen of one dose administered every 28 days plus/minus 4 days; a dosing regimen of "about once monthly" refers to a dosing regimen of one dose administered every 30 days plus/minus 4 days; a dosing regimen of "about once every 5 weeks" refers to a dosing regimen of one dose administered every 35 days plus/minus 5 days; and a dosing regimen of "about once every 6 weeks" refers to a dosing regimen of one dose administered every 42 days plus/minus 6 days.

As used herein the term "about" in connection with a particular drug dose shall have the meaning of a drug dose in the range of plus/minus 10% w/w, preferably plus/minus 5% w/w or less, of the nominal drug dose. By way of example, a nominal dose of about 0.01 mg active ingredient may contain from 0.009 to 0.011 mg, preferably from 0.0095 to 0.0105 active ingredient per dose, whereas a nominal dose of about 0.5 mg active ingredient may contain from 4.5 to 5.5 mg, preferably from 4.75 to 5.25 active ingredient per dose.

As used herein, the term "elimination half-life" of a drug refers to the time required for the concentration of the drug in serum or plasma, to decrease by half, in vivo, for example due to degradation and/or clearance or sequestration by natural mechanisms. When determined experimentally by measuring drug concentration in plasma samples drawn at various and successive times after drug intake, this parameter is named "apparent elimination half-life", designated T½. Methods for pharmacokinetic analysis and determination of drug half-life will be familiar to those skilled in the art. Pharmacokinetic parameters such as "apparent elimination half-life" T½ and area under the curve (AUC) can be determined from a curve of plasma or serum concentration of the drug against time. In particular, the following pharmacokinetic definitions shall apply:

$AUC_{0-t}$ the AUC from time zero to time 't', where t is the last sampling time point [mass×time×volume$^{-1}$].

$AUC_{0-\infty}$ the AUC from time zero to infinity [mass×time×volume$^{-1}$].

$C_{max}$ the maximum (peak) observed plasma, blood, serum, or other body fluid drug concentration after single dose administration [mass×volume$^{-1}$].

$C_{last}$ The last measurable plasma, blood, serum, or other body fluid drug concentration CL the total body clearance of drug from the plasma [volume×time$^{-1}$].

Clearance values from other body fluids may be noted by use of proper subscripts, for example $CL_b$ refers to clearance from the blood and $CL_u$ clearance of unbound drug from the plasma. If the clearance is following extravascular dose and bioavailability parameter is not known, then the notation should be CL/F.

t time after drug administration [time]

$T_{last}$ time of last measurable concentration (when $C_{last}$ occurs)

$T_{max}$ the time to reach maximum (peak) plasma, blood, serum, or other body fluid drug concentration after single dose administration [time].

$T_{1/2}$ the elimination half-life associated with the terminal slope ($\lambda_z$) of a semilogarithmic concentration-time curve [time].

The drug concentration in plasma and/or serum samples can be determined by a number of different ways, e.g. HPLC or LC-MS/MS analyses. In one embodiment, the concentration of 4,4'-[fluoro-(1-H-1,2,4-triazol-1-yl)methylene]bisbenzonitrile in plasma is analyzed using a validated LC-MS/MS method with a lower limit of quantification (LLOQ) at 0.1 ng/mL or better. In another embodiment, the concentration of 4,4'-[fluoro-(1-H-1,2,4-triazol-1-yl)methylene]bisbenzonitrile in human plasma is analyzed using a validated LC-MS/MS method with a lower limit of quantification (LLOQ) at 0.025 ng/mL.

As used herein the term "about" in connection with a particular apparent elimination half-life shall have the meaning of an apparent elimination half-life in the range of plus/minus 20% w/w, preferably plus/minus 15% w/w or less, of the particularly mentioned apparent elimination half-life. In one embodiment, the term "about" in connection with a particular apparent elimination half-life shall have the meaning from "plus/minus 2 day" for an apparent elimination half-life of about 14 days to "plus/minus 5 days" for an apparent elimination half-life of about 30 days. An apparent elimination half-life of about 20 days shall refer to an apparent elimination half-life of 20 days "plus/minus 3 days", an apparent elimination half-life of about 25 days shall refer to an apparent elimination half-life of 25 days "plus/minus 4 days", and an apparent elimination half-life of about 30 days shall refer to an apparent elimination half-life of 30 days "plus/minus 5 days".

As used herein, the term "treatment period" refers to the length of the time period wherein the compound is administered to a patient. The phrase "a treatment period of at least about two months" shall have the meaning the compound shall be administered continuously (according to the dosing regimen) for at least 2 months, but potentially also longer, e.g. continuously for at least 3, 4, 5, 6, 7, 8, 9, 10, 11, etc months. In general, treatment could also exceed a time period of 12 months, i.e. the compound might be considered for continuous long term treatment. However, there might be circumstances under which shorter treatment periods or intermittent treatment periods are advisable.

As used herein the term "about" in connection with a particular length of treatment period shall have the meaning of "plus/minus 5 days" for every month of treatment, i.e. a treatment period of "about two months" shall refer to a treatment period of two months plus/minus 10 days, a treatment period of "about three months" shall refer to a treatment period of three months plus/minus 15 days, etc.

DETAILED DESCRIPTION OF THE INVENTION

The aromatase inhibitor 4,4'-[fluoro-(1-H-1,2,4-triazol-1-yl)methylene]bisbenzonitrile is now shown to have the potential to address specifically the needs of male patients being in need of increased testosterone levels, in particular male patients being overweight or obese and/or suffering from hypogonadism, especially hypogonadotropic hypogonadism.

The aromatase enzyme catalyzes the conversion of endogenous testosterone into estradiol and is furthermore in particular present in excess adipose tissue. Elevated serum estradiol levels may inhibit pituitary LH secretion and thereby reduce serum testosterone level. Administration of 4,4'-[fluoro-(1-H-1,2,4-triazol-1-yl)methylene]bisbenzonitrile, a highly selective aromatase inhibitor, shows dose dependent reduction of the conversion of testosterone to estrone, estrone sulfate and estradiol, and thereby an increase of endogenous testosterone levels.

Whereas conventional medical therapies for hypogonadism work by supplementing testosterone or administration of HCG or gonadotropins, administration of 4,4'-[fluoro-(1-H-1,2,4-triazol-1-yl)methylene]bisbenzonitrile inhibits testosterone conversion by aromatase, especially local testosterone conversion by aromatase in fat tissue, especially targeting overweight or obese patients. Since testosterone deficiency in men, in particular in men with overweight or obesity is often associated with metabolic abnormalities including insulin resistance, glucose intolerance, and lipid abnormalities, contributing to an increased incidence of metabolic syndrome, type II diabetes and cardiovascular diseases, administration of 4,4'-[fluoro-(1-H-1,2,4-triazol-1-yl)methylene]-bisbenzonitrile is considered to be especially suited for this patient population.

Accordingly, administration of 4,4'-[fluoro-(1-H-1,2,4-triazol-1-yl)methylene]-bisbenzonitrile leads to improved treatment efficacy in overweight or obese male patients with confirmed hypogonadotropic hypogonadism via inhibition of testosterone to estrogen conversion at all sites, especially however in the adipose tissue. Administration is considered especially useful if the patients suffer from one or more disorders selected from insulin resistance, glucose intolerance and dyslipidaemia. Increasing testosterone levels by administration of 4,4'-[fluoro-(1-H-1,2,4-triazol-1-yl)methylene]bisbenzonitrile is considered especially useful for improving insulin sensitivity, improving glucose metabolism and/or improving the lipid profile in this patient population.

In particular, administration of 4,4'-[fluoro-(1-H-1,2,4-triazol-1-yl)methylene]-bisbenzonitrile is considered to effectively improve insulin sensitivity in the overweight or obese male patient with hypogonadotropic hypogonadism by normalizing testosterone levels. In addition, the treatment according to the invention is thought to improve insulin sensitivity with improved glycaemic control (as measurable by lower postprandial glucose, lower HbA1c levels), to prevent progression of pre-diabetes to diabetes, to support the reduction of body fat mass and to improve body lean mass.

Furthermore, administration of 4,4'-[fluoro-(1-H-1,2,4-triazol-1-yl)methylene]-bisbenzonitrile is considered to prevent, improve or treat other conditions associated with hypogonadism including, but is not limited to, decreased libido, decreased spontaneous erections, erectile dysfunction, decreased fertility, loss of body hair, reduced shaving, lack of energy, fatigue, impaired cognition, depression, changes in mood, low bone mineral density, increased risk of fractures, decreased muscle mass, decreased muscle strength, increased abdominal fat mass, limited body performance capacity and cardiovascular risks.

Administration of 4,4'-[fluoro-(1-H-1,2,4-triazol-1-yl)methylene]-bisbenzonitrile according to the invention is also considered useful when the male patient is in need of increased muscle mass and strength, when the patient is in need of a normalized body composition, when the patient is in need of a decrease in abdominal fat mass (as assessed by waist circumference and/or waist/hip circumference ratio), when the patient is in need of an improved sexual function and desire, when the patient is in need of increased fertility, and/or when the patient is in need of increased bone mineral density.

4,4'-[fluoro-(1-H-1,2,4-triazol-1-yl)methylene]bisbenzonitrile is a potent and selective inhibitor of aromatase. The $IC_{50}$ and $K_i$ values for aromatase inhibition were determined in the microsomal fraction of human placenta and showed that the compound is a competitive inhibitor with an $IC_{50}$ of approximately 6.2 nM [Batzl-Hartmann et al, 1994].

Toxicologic studies of 4,4'-[fluoro-(1-H-1,2,4-triazol-1-yl)methylene]bisbenzonitrile in female and male dogs showed that there was no consistent difference in exposure (AUC and $C_{max}$) between male and female dogs. $T_{max}$ values were ranging from 1 h to 24 hrs post dose. Generally, the inter-animal variability in $C_{max}$ levels was small. In general, following weekly oral dosing of 4,4'-[fluoro-(1-H-1,2,4-triazol-1-yl)methylene]bisbenzonitrile for 4 or 22 weeks, the mean plasma exposure to the compound was similar to that observed after a single dose at all dose levels tested, indicating there is no drug accumulation. An increase in exposure (AUC and $C_{max}$) was generally proportional to the dose increase for male and female dogs after single and multiple doses of 4,4'-[fluoro-(1-H-1,2,4-triazol-1-yl)methylene]bisbenzonitrile at all dose levels tested. Furthermore, measurement of testosterone levels in the serum of male dogs after 1, 4 and 12 weeks of dosing showed dramatically elevated testosterone levels at all dose levels demonstrating the potential of 4,4'-[fluoro-(1-H-1,2,4-triazol-1-yl)methylene]bisbenzonitrile.

In humans, the compound was initially studied in a single, ascending dose protocol in human female volunteers to assess safety and tolerability (see Example 3), as well as an $^{14}$C-4,4'-[fluoro-(1-H-1,2,4-triazol-1-yl)methylene]bisbenzonitrile ADME study (Example 4) to determine tissue half life of the drug. The first study showed that the median $T_{max}$ occurred within 1 hour of ingestion, and that the half life was extremely long, approximately 25 days at doses above 0.01 mg. In the human ADME study in postmenopausal women, the compound accumulated in fat tissue at a 1-3 fold rate in comparison to the exposure as plasma, with the same clearance pattern. Given that the excess aromatase activity in overweight or obese hypogonadotropic men with hypogonadism occurs primarily in the adipose tissue, 4,4'-[fluoro-(1-H-1,2,4-triazol-1-yl)methylene]bisbenzonitrile is considered to have the ideal pharmacokinetic distribution profile for optimal suppression of aromatase activity. Suppression of adipose aromatase activity is assumed to result in reduction of serum estradiol, increase of LH and FSH, and increase in serum testosterone.

The ongoing study of 4,4'-[fluoro-(1-H-1,2,4-triazol-1-yl)methylene]bisbenzonitrile for the treatment of obese hypogonadotropic male patients with hypogonadism shows the effectiveness of this new treatment regimen in the target patient population (Example 5).

An effective amount of 4,4'-[fluoro-(1-H-1,2,4-triazol-1-yl)methylene]bisbenzonitrile for the treatment of overweight or obese hypogonadotropic male patients with hypogonadism is considered to be in the range from about 0.0005 mg to about 5.0 mg, preferably from about 0.0005 mg to about 2.0 mg, preferably from about 0.001 mg to about 1.0 mg, more preferably from about 0.005 mg to about 0.5 mg, most preferably from about 0.01 mg to about 0.1 mg, from about 0.005 mg to less than 0.05 mg 4,4'-[fluoro-(1-H-1,2,4-triazol-1-yl)methylene]bisbenzonitrile per dose. In one embodiment, the effective dose is considered to be higher than 0.0005 mg, 0.001 mg, 0.005 mg, or 0.01 mg, but lower than 2.0 mg, 1.0 mg, 0.5 mg, 0.1 mg, or 0.05 mg 4,4'-[fluoro-(1-H-1,2,4-triazol-1-yl)methylene]bisbenzonitrile per dose. In an alternative embodiment, the effective dose is considered to be in the range from about 0.005 mg to less than 0.01 mg.

In another embodiment it might be considered to start treatment with a defined loading dose of 4,4'-[fluoro-(1-H-1,2,4-triazol-1-yl)methylene]bisbenzonitrile, and then to assess the testosterone response after a single dose (e.g. after 1, 2, 3, 4, 5 or 6 days or even more than 6 days after a single dose), and adjust the next dose according to the treatment regimen (e.g. daily dose, weekly dose, or monthly dose) up or down based on the acute testosterone response. In one embodiment of the invention the loading dose of 4,4'-[fluoro-(1-H-1,2,4-triazol-1-yl)methylene]bisbenzonitrile dose is 0.3 mg followed by a weekly dose of 0.1 mg.

The present invention discloses an optimized treatment regimen providing relief of the testosterone deficit driven symptoms of hypogonadism with additional beneficiary treatment effects. The development of an aromatase inhibitor especially suited for hypogonadal male patients provides a novel treatment option for this disease. The present invention especially addresses overweight or obese hypogonadotropic hypogonadal male patients with associated symptoms and disorders.

Accordingly, the present invention concerns the use of the compound 4,4'-[fluoro-(1-H-1,2,4-triazol-1-yl)methylene]bisbenzonitrile in the treatment of a male patient in need of increased testosterone levels. In one embodiment the present invention concerns the use of the compound 4,4'-[fluoro-(1-H-1,2,4-triazol-1-yl)methylene]bisbenzonitrile in the treatment of an obese or overweight male patient.

In one embodiment the present invention concerns the use of the compound 4,4'-[fluoro-(1-H-1,2,4-triazol-1-yl)methylene]bisbenzonitrile in the treatment of hypogonadism in a male patient, preferably hypogonadotropic hypogonadism in a male patient, most preferably hypogonadotropic hypogonadism in an overweight or obese male patient.

Furthermore, the present invention concerns the use of the compound 4,4'-[fluoro-(1-H-1,2,4-triazol-1-yl)methylene]bisbenzonitrile in the treatment of a male patient in need of increased testosterone levels, wherein the compound is provided in a form comprising from about 0.0005 mg to about 5.0 mg, preferably from about 0.0005 mg to about 2.0 mg 4,4'-[fluoro-(1-H-1,2,4-triazol-1-yl)methylene]-bisbenzonitrile per dose and is for administration according to a dosing regimen having a dosing periodicity ranging from about once daily to about once every 60 days.

In the context of the present invention the wording "the use of the compound 4,4'-[fluoro-(1-H-1,2,4-triazol-1-yl)methylene]bisbenzonitrile in the treatment of ( . . . )" shall be construed either as "the compound 4,4'-[fluoro-(1-H-1,2,4-triazol-1-yl)methylene]bisbenzonitrile for use in the treatment of ( . . . )" or as "use of the compound 4,4'-[fluoro-(1-H-1,2,4-triazol-1-yl)methylene]bisbenzonitrile for the manufacture of a medicament for the treatment of ( . . . )". Both meanings are equally contemplated within the scope of the invention.

In one embodiment, the patient is a male human patient, preferably an overweight or obese male human patient. Treatment of overweight or obese male human patients is most preferred for hypogonadism and associated conditions; however treatment of other male patients being in need of increased testosterone might also be contemplated if appropriate.

In one embodiment, the male patient in need of increased testosterone levels suffers from hypogonadism, preferably hypogonadotropic hypogonadism. In particular, the present invention relates to the treatment of hypogonadotropic hypogonadism in obese or overweight male human patients.

In one embodiment, the present invention relates to the use of the compound in the above mentioned patient population for increasing, preferably normalizing testosterone levels. In particular, increasing, preferably normalizing testosterone levels in an overweight or obese male patient with hypogonadotropic hypogonadism is considered.

A low serum testosterone concentration predicts or is associated with the metabolic syndrome and type II diabetes, in particular in men with overweight or obesity.

Accordingly, in one embodiment, the present invention relates to the use of the compound for the prevention or treatment of one or more disorders selected from metabolic syndrome, type II diabetes, obesity and cardiovascular disease in the above mentioned patients, preferably in patients suffering from hypogonadism or hypogonadotropic hypogonadism, preferably in overweight or obese patients suffering from hypogonadism or hypogonadotropic hypogonadism.

In another embodiment, the present invention relates to the use of the compound for the prevention or treatment of one or more disorders selected from insulin resistance, glucose intolerance and dyslipidaemia in the above mentioned patients, preferably in patients suffering from hypogonadism or hypogonadotropic hypogonadism, preferably in overweight or obese patients suffering from hypogonadism or hypogonadotropic hypogonadism.

In a further embodiment, the present invention relates to the use of the compound for the improvement of insulin sensitivity and/or glucose metabolism and/or the lipid profile in the above mentioned patients, preferably in patients suffering from hypogonadism or hypogonadotropic hypogonadism, preferably in overweight or obese patients suffering from hypogonadism or hypogonadotropic hypogonadism.

In addition, the present invention relates to the use of the compound for the prevention or treatment of one or more disorders selected from the group consisting of decreased libido, decreased spontaneous erections, erectile dysfunction, decreased fertility, loss of body hair, reduced shaving, lack of energy, fatigue, impaired cognition, depression, changes in mood, low bone mineral density, increased risk of fractures, decreased muscle mass, decreased muscle strength, increased abdominal fat mass and limited body performance capacity, wherein the patient is in need of increased testosterone levels. In particular, the patient has hypogonadism or hypogonadotropic hypogonadism, preferably overweight or obese hypogonadotropic hypogonadism.

In further embodiments of the invention relating to the use of the compound, as herein defined, the compound is provided in a form comprising from about 0.0005 mg to about 5.0 mg, preferably from about 0.0005 mg to about 2.0 mg 4,4'-[fluoro-(1-H-1,2,4-triazol-1-yl)methylene]bisbenzonitrile per dose. E.g. the compound can be provided in a form comprising about 0.0005 mg, about 0.001 mg, about 0.005 mg, about 0.006 mg, about 0.007 mg, about 0.008 mg, about 0.009 mg, about 0.01 mg, about 0.015 mg, about 0.02 mg, about 0.025 mg, about 0.03 mg, about 0.035 mg, about 0.04 mg, about 0.45 mg, about 0.05 mg, about 0.06 mg, about 0.07 mg, about 0.08 mg, about 0.09 mg, about 0.1 mg, about 0.15 mg, about 0.2 mg, about 0.25 mg, about 0.3 mg, about 0.35 mg, about 0.4 mg, about 0.45 mg, about 0.5 mg, about 0.75 mg, about 1 mg or at maximum about 2 mg or 5 mg 4,4'-[fluoro-(1-H-1,2,4-triazol-1-yl)methylene]bisbenzonitrile per dose. E.g. the compound can be provided in a form comprising about 0.1 mg 4,4'-[fluoro-(1-H-1,2,4-triazol-1-yl)methylene] bisbenzonitrile per dose. In one embodiment, the compound is provided in a form comprising about 0.01 mg 4,4'-[fluoro-(1-H-1,2,4-triazol-1-yl)methylene]bisbenzonitrile per dose.

In particular, the compound is provided in a form comprising from about 0.0005 mg to about 0.5 mg 4,4'-[fluoro-(1-H-1,2,4-triazol-1-yl)methylene]bisbenzonitrile per dose, preferably in a form comprising from about 0.001 mg to about 1.0 mg, more preferably from about 0.005 mg to about 0.5 mg, most preferably from about 0.01 mg to about 0.1 mg, or from about 0.005 mg to less than 0.05 mg 4,4'-[fluoro-(1-H-1,2,4-triazol-1-yl)methylene]bisbenzonitrile per dose.

In one embodiment, the compound is to be administered according to a dosing regimen having a dosing periodicity ranging from one dose administered about once daily, preferably once weekly or once biweekly, to one dose administered about once every 60 days. In one embodiment, the present invention relates to the use of the compound according to a dosing regimen with a dosing periodicity of one dose administered about once daily, about once every 2 days, about once every 5 days, about once weekly, about once biweekly, about once every 3 weeks, about once every 4 weeks, about once monthly and about once every 6 weeks, preferably about once weekly or once biweekly.

In further embodiments of the invention relating to the use of the compound, the compound is provided in any form as set out above comprising from about 0.0005 mg to about 1.0 mg per dose, being administered according to a dosing regimen having a dosing periodicity selected from about once daily, about once every two days, about once weekly, about once every 10 days, about once biweekly, about once every 4 weeks, about once monthly and about once every 6 weeks. In particular, the compound is provided in a form comprising from about 0.01 mg to about 0.1 mg 4,4'-[fluoro-(1-H-1,2,4-triazol-1-yl)methylene]bisbenzonitrile per dose, e.g. comprising about 0.01 mg, about 0.02 mg, about 0.03 mg, about 0.04 mg, about 0.05 mg, about 0.06 mg, about 0.07 mg, about 0.08 mg or about 0.09 mg per dose, preferably 0.1 mg per dose, being administered according to a dosing regimen having a dosing periodicity of about once weekly or once biweekly or about every 4 weeks or about once monthly.

In some embodiments, the compound is to be administered on an intermittent basis. In these embodiments the compound, e.g. a dose that comprises from about 0.0005 mg to about 5.0 mg, preferably from about 0.0005 mg to about 2.0 mg 4,4'-[fluoro-(1-H-1,2,4-triazol-1-yl)methylene]bisbenzonitrile, is administered to a patient for at least one day, optionally followed by further doses according to a dosing regimen as described herein above, for example in a dosing regimen having a dosing periodicity ranging from about once daily to about once every 60 days, followed by a period of no dosing for a period of about one day to about 6 month or longer, for example for a period of about one day, of about two days, of about one week, of about 10 days, of about two weeks, of about 4 weeks, of about one month, of about 6 weeks, of about 2 month, of about 3 months, of about 4 month, of about 5 month or of about 6 month.

In one aspect of the invention, the compound 4,4'-[fluoro-(1-H-1,2,4-triazol-1-yl)methylene]bisbenzonitrile is provided for oral administration.

In another aspect of the invention, the compound 4,4'-[fluoro-(1-H-1,2,4-triazol-1-yl)methylene]bisbenzonitrile when administered to the patient, shows an apparent elimination half-life of at least about 14 days, at least about 20 days, and at least about 25 days. In one embodiment, the compound may even show an apparent elimination half-life of at least about 30 days or even at least 35 days. In another embodiment, the compound may show an apparent elimination half-life of approximately 22 to 29 days. In another embodiment, the compound may show an apparent elimination half-life of approximately 23 to 27 days. This extraordinary long half-life in humans was demonstrated by way of Examples 3 and 4. The results observed were completely unexpected in view of the previous rat experiments showing a half-life of about a week [Batzl-Hartmann et al, 1994 and Bhatnagar et al, 1996]. This surprising extremely long half-life of the compound in humans gives rise to the particular dosing scheduled of the invention.

In one embodiment of the invention, the compound 4,4'-[fluoro-(1-H-1,2,4-triazol-1-yl)methylene]bisbenzonitrile is to be administered to the patient as defined herein for a treatment period of at least about two months, preferably at least about three months. In another embodiment, the administration of the compound as defined herein can extend even longer and be provided for continuous treatment.

In addition, the present invention refers to a method for the treatment of a male patient in need of increased testosterone levels comprising administering to said patient an effective amount of 4,4'-[fluoro-(1-H-1,2,4-triazol-1-yl)methylene]bisbenzonitrile.

Furthermore, the invention relates to a method for the treatment of a male patient in need of increased testosterone levels comprising administering to said patient an effective amount of 4,4'-[fluoro-(1-H-1,2,4-triazol-1-yl)methylene]bisbenzonitrile in a dose from about 0.0005 mg to about 5.0 mg, preferably in a dose from about 0.0005 mg to about 2.0 mg in a dosing regimen having a dosing periodicity ranging from about once daily to about once every 60 days.

In one embodiment, said male patient is obese. In another embodiment said male patient is overweight. In another embodiment, the method is for the treatment of hypogonadism or hypogonadotropic hypogonadism. In particular, the method of treatment is for the treatment of hypogonadism in an overweight or obese male patient, preferably for the treatment of hypogonadotropic hypogonadism in an overweight or obese male patient.

Said male patient being in need of increased testosterone levels may also be in need of the prevention or treatment of one or more disorders selected from metabolic syndrome, type II diabetes, obesity and cardiovascular disease. In a further embodiment said patient is in need of the prevention or treatment of one more disorders selected from insulin resistance, glucose intolerance and dyslipidaemia. In particular, the patient is in need of improved insulin sensitivity, or in need of improved glucose metabolism, or in need of an improved lipid profile.

Said male patient being in need of increased testosterone levels may also be in need of the prevention or treatment of one or more disorders selected from the group consisting of decreased libido, decreased spontaneous erections, erectile dysfunction, decreased fertility, loss of body hair, reduced shaving, lack of energy, fatigue, impaired cognition, depression, changes in mood, low bone mineral density, increased risk of fractures, decreased muscle mass, decreased muscle strength, increased abdominal fat mass and limited body performance capacity.

In a further embodiment, said male patient being in need of increased testosterone levels and/or suffering from hypogonadism is in need of increased muscle mass and strength, in need of a normalized body composition, in need of a decrease in abdominal fat mass, in need of an improved sexual function and desire, in need of increased fertility, or in need of increased bone mineral density.

Furthermore, the invention relates to a method for the treatment of a male patient in need of increased testosterone levels comprising administering to said patient an effective amount of 4,4'-[fluoro-(1-H-1,2,4-triazol-1-yl)methylene]bisbenzonitrile, wherein the administration of the compound increases the testosterone level by at least 10% over the testosterone level prior to administration of the compound. In a further embodiment, administration of the compound normalizes testosterone levels.

All embodiments set out above for the use of the compound 4,4'-[fluoro-(1-H-1,2,4-triazol-1-yl)methylene]bisbenzonitrile for the treatment of one of the aforementioned diseases shall apply mutatis mutandis for the above mentioned method of treatments of the respective diseases with this compound.

Accordingly, an effective amount of 4,4'-[fluoro-(1-H-1,2,4-triazol-1-yl)methylene]bisbenzonitrile can be from about 0.0005 mg to about 5.0 mg per dose, from about 0.0005 mg to about 2.0 mg per dose, from about 0.001 mg to about 1.0 mg per dose, or from about 0.005 mg to about 0.5 mg per dose, e.g. 0.001 mg, about 0.005 mg, about 0.006 mg, about 0.007 mg, about 0.008 mg, about 0.009 mg, about 0.01 mg, about 0.015 mg, about 0.02 mg, about 0.025 mg, about 0.03 mg, about 0.035 mg, about 0.04 mg, about 0.45 mg, about 0.05 mg, about 0.06 mg, about 0.07 mg, about 0.08 mg, about 0.09 mg, about 0.1 mg, about 0.15 mg, about 0.2 mg, about 0.25 mg, about 0.3 mg, about 0.35 mg, about 0.4 mg, about 0.45 mg, about 0.5 mg per dose. In particular, an effective amount of 4,4'-[fluoro-(1-H-1,2,4-triazol-1-yl)methylene]-bisbenzonitrile is about 0.01 mg per dose.

An effective amount of 4,4'-[fluoro-(1-H-1,2,4-triazol-1-yl)methylene]bisbenzonitrile selected from about 0.0005 mg to about 5.0 mg per dose, preferably from about 0.0005 mg to about 2.0 mg per dose can be administered according to a dosing regimen having a dosing periodicity ranging from about once daily to about once every 60 days or ranging from about once weekly to about once monthly.

More specifically, an effective amount of 4,4'-[fluoro-(1-H-1,2,4-triazol-1-yl)methylene]bisbenzonitrile from about 0.0005 mg to about 5.0 mg per dose, preferably from about 0.0005 mg to about 2.0 mg per dose, more preferably from about 0.01 mg to about 0.1 mg per dose can be administered according to a dosing regimen having a dosing periodicity selected from about once daily, once every two days, once weekly, about once every 10 days, about once biweekly, about once every 4 weeks, about once monthly and about once every 6 weeks. An effective amount of 4,4'-[fluoro-(1-H-1,2,4-triazol-1-yl)methylene]bisbenzonitrile from about 0.01 mg to about 0.1 mg per dose (e.g. about 0.01 mg, about 0.02 mg, about 0.03 mg, about 0.04 mg, about 0.05 mg, about 0.06 mg, about 0.07 mg, about 0.08 mg or about 0.09 mg per dose) can be administered according to a dosing regimen having a dosing periodicity of about once weekly or once biweekly or once every 4 weeks or once monthly.

In another embodiment, the compound shows when administered according to the treatment method of the invention an apparent elimination half-life of at least about 14 days, preferably of at least about 20 days, more preferably of at least about 25 days, and most preferably of at least about 30 days.

In a further embodiment, the invention relates to a method for the treatment of a male patient in need of increased testosterone levels as defined herewithin comprising administering to said patient a single dose of 4,4'-[fluoro-(1-H-1,2,4-triazol-1-yl)methylene]bisbenzonitrile, wherein said dose results in an increased effective blood concentration of testosterone over a period of time from 3 to 30 days. In particular, the serum concentration of testosterone is increased by at least 10% over the serum testosterone concentration prior to administration of the compound.

The compound 4,4'-[fluoro-(1-H-1,2,4-triazol-1-yl)methylene]bisbenzonitrile may be provided in various formulations such as parentally (e.g. aqueous or oily suspensions) or orally (e.g., tablets, powders, capsules, granules, aqueous or oily suspensions). Preferably, the compound is provided in an orally available formulation to be administered according to the described dosing regimen. However, slow release formulation or depot or transdermal formulations could also be used to administer the compound.

Thus, according to a further embodiment of the invention, there is provided an oral pharmaceutical formulation comprising from about 0.0005 mg to about 5.0 mg, preferably from about 0.0005 mg to about 2.0 mg 4,4'-[fluoro-(1-H-1,2,4-triazol-1-yl)methylene]bisbenzonitrile per dose, optionally in combination with one or more pharmaceutically acceptable excipients.

In one embodiment, the pharmaceutical composition comprises from about 0.001 mg to about 1.0 mg, preferably from about 0.005 mg to about 0.5 mg, more preferably from about 0.01 mg to about 0.1 mg, e.g. about 0.02 mg, about 0.03 mg, about 0.04 mg, about 0.05 mg, about 0.06 mg, about 0.07 mg, about 0.08 mg, or about 0.09 mg, most preferably about 0.01 mg 4,4'-[fluoro-(1-H-1,2,4-triazol-1-yl)methylene]bisbenzonitrile per dose.

For preparing pharmaceutical formulations of the invention, inert, pharmaceutically acceptable excipients can be added to the components of the composition which can either be solid or liquid. Solid form preparations comprise powders, tablets, dispersible granules, capsules and cachets.

A solid pharmaceutically acceptable excipient can be one or more substances which may act as carriers, diluents, flavoring agents, solubilizers, lubricants, suspending agents, binders, and/or tablet disintegrating agents; it can also be an encapsulating material.

In powders, a finely divided solid excipient is provided in a mixture with the finely divided active component. In tablets, the active component is mixed with an excipient having the necessary binding properties in suitable proportions and compacted in the shape and size desired.

Suitable excipients include magnesium carbonate, magnesium stearate, talc, lactose, lactose monohydrate, sugar, pectin, dextrin, starch, tragacanth, microcrystalline cellulose, methyl cellulose, sodium carboxymethyl cellulose, corn starch, colloidal anhydrous Silica, titanium dioxide, a low-melting wax, cocoa butter, and the like.

The term formulation is intended to include the mixture of the active component(s) with encapsulating material as a carrier providing a capsule in which the active compound (with or without other carriers) is surrounded by a carrier which is thus in association with it. Similarly, cachets are included. Tablets, powders, cachets, and capsules can be used as solid dosage forms suitable for oral administration.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical formulation can be in unit dosage form. In such form, the composition is divided into unit doses containing appropriate quantities of the active component(s). The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

In a further embodiment, the invention pertains to an oral pharmaceutical composition as set out above which shows, when administered to the patient, an apparent elimination half-life of 4,4'-[fluoro-(1-H-1,2,4-triazol-1-yl)methylene]bisbenzonitrile of at least about 14 days, preferably of at least about 20 days, more preferably of at least about 25 days and most preferably of at least about 30 days. In one embodiment, the compound may even show an apparent elimination half-life of at least about 30 days. In another embodiment, the compound may show an apparent elimination half-life of approximately 22 to 29 days.

In another embodiment, the invention refers to a kit of parts comprising: (i) a pharmaceutical composition comprising the compound 4,4'-[fluoro-(1-H-1,2,4-triazol-1-yl)methylene]bisbenzonitrile as defined herewithin; together with (ii) instructions how to administer said pharmaceutical composition for the treatment of a male patient in need of increased testosterone levels, in particular for the treatment of hypogonadism or hypogonadotropic hypogonadism in a male patient, preferably an overweight or obese male patient. These instructions will explain in detail the dosing regimen how the compound is to be administered, as set out in more detail below.

In a further embodiment, the invention refers to a kit of parts comprising: (i) a pharmaceutical composition comprising from about 0.0005 mg to about 5.0 mg, preferably from about 0.0005 mg to about 2.0 mg, preferably from about 0.001 mg to about 1.0 mg, more preferably from about 0.005 mg to about 0.5 mg, most preferably from about 0.01 mg to about 0.1 mg, or from about 0.005 mg to less than 0.01 mg 4,4'-[fluoro-(1-H-1,2,4-triazol-1-yl)methylene]bisbenzonitrile per dose; together with (ii) instructions how to administer said pharmaceutical composition. These instructions will explain in detail the dosing regimen how the compound is to be administered, as set out in more detail below.

In a further embodiment, the kits of parts as defined here within comprise instructions stating that pharmaceutical composition is for the treatment of a male patient in need of increased testosterone levels, in particular for the treatment of hypogonadism or hypogonadotropic hypogonadism in a male patient, preferably an overweight or obese male patient. In particular, the instructions state that the pharmaceutical composition is to be administered according to a dosing regimen having a dosing periodicity ranging from about once daily to about once every 60 days, preferably selected from a dosing regimen having a dosing periodicity of about once every 2 days, about once every 5 days, about once weekly, about once biweekly, about once every 3 weeks, about once every 4 weeks, about once monthly and about once every 6 weeks, preferably about once weekly or once biweekly.

In another embodiment, the instructions of the kits of parts are provided either as a leaflet or in the form of a printed matter on the packaging of the pharmaceutical composition.

This invention is further illustrated by the following examples which should not be construed as limiting.

EXAMPLES

Example 1

Preparation of 4,4'-[fluoro-(1-H-1,2,4-triazol-1-yl)methylene]bisbenzonitrile

The following example describes a method for the synthesis of 4,4'-[fluoro-(1-H-1,2,4-triazol-1-yl)methylene]bisbenzonitrile (also known as 4-[α-4-Cyanophenyl)-α-fluoro-1-1,2,4-triazolyl)-methyl]-benzonitrile or CGP47645) as disclosed within Lang et al., U.S. Pat. No. 5,637,605:

A solution of 0.8 mmol of potassium hexamethyldisilazane in 1.6 ml of toluene is diluted with 5 ml of THF and, after cooling to −78° C., a solution of 190 mg of 4-[α-(4-cyanophenyl)-1-(1,2,4-triazolyl)methyl]-benzonitrile (see EP-A-236 940, Ex. 20a) in 3 ml of THF is added thereto. After stirring for 1 hour at the same temperature, there are added dropwise to the dark-red solution 301 mg of N-fluoro-dimethylsaccharinsultam in 3 ml of THF. After a further 1.5 hours at −78° C., the reaction mixture is heated to room temperature within 1 hour and poured onto a saturated solution of ammonium chloride in water and then extracted with methylene chloride. Drying over magnesium chloride and concentration of the solvent by evaporation yields the crude product which is purified by means of flash-chromatography (SiO$_2$, hexane/ethyl acetate 9:1, 4:1 to 1:1). TLC (SiO$_2$, CHCl$_3$/methanol 9:1, Rf=0.85); IR (KBr): 2220 cm$^{-1}$; $^1$H-NMR (CDCl$_3$): δ (ppm)=7.46 and 7.76 (8H, m), 8.07 (1H, s), 8.16 (1H, s).

All disclosure relevant to the preparation of 4-[α-4-Cyanophenyl)-α-fluoro-1-1,2,4-triazolyl)-methyl]-benzonitrile described in Lang et al., U.S. Pat. No. 5,376,669 is hereby incorporated by reference herein.

The above paragraph refers to EP-A-236 940, Ex. 20a. The U.S. equivalent to EP-236 940 is Bowman, U.S. Pat. No. 4,749,713. Example 20 (a) of EP-A-236 940 (equivalent U.S. Pat. No. 4,749,713) states that 4-[1-(1,2,4-Triazolyl)-methyl]-benzonitrile is reacted with potassium tert-butoxide and 4-fluorobenzonitrile according to the procedure in Example 2 of U.S. Pat. No. 4,749,713 to yield 4-[α-(4-cyanophenyl)-1-(1,2,4-triazolyl)-methyl]benzonitrile, m.p. 181° C.-183° C.

The procedure of Example 2 of U.S. Pat. No. 4,749,713 provides that: A suspension of potassium tert-butoxide (61.6 g) in dimethylformamide (500 mL) is stirred and cooled to −10° C. (ice-salt bath), and a solution of 4-(1-imidazolylmethyl)-benzonitrile (45.6 g) in dimethylformamide (250 mL) is added so that the reaction temperature remains below 0° C. The resulting solution is stirred at 0° C. for 0.5 hour and then a solution of 4-fluorobenzonitrile (38.3 g) in dimethylformamide (100 mL) is added while keeping reaction temperature below 5° C. After 0.75 hour, the reaction mixture is neutralized to pH 7 by addition of sufficient 3N hydrochloric acid and the bulk of the solvents are then removed under reduced pressure. The residue is diluted with water (500 mL) and the crude product is extracted into ethyl acetate (3×200 mL). The combined extracts are then extracted with 3N hydrochloric acid (3×150 mL) and, after washing the latter acid extracts with ethyl acetate (100 mL), the solution is made basic (pH 8) with 6N ammonium hydroxide and the product is again extracted into ethyl acetate (3×150 mL). The combined extracts are dried (MgSO$_4$), decolorized by treatment with charcoal, and then evaporated to give crude 4-[α-(4-cyanophenyl)-1-imidazolylmethyl]-benzonitrile as an oil. This material is dissolved in isopropanol (250 mL) and the warm solution is stirred with succinic acid (14.4 g). Upon dilution with diethyl ether (100 mL) and stirring at ambient temperature, the hemisuccinate salt separates. The salt is filtered off, washed with a little cold isopropanol and then air dried to afford 4-[α-(4-cyanophenyl)-1-imidazolylmethyl]-benzonitrile hemisuccinate, m.p. 149° C.-150° C. The hemifumarate salt has m.p. 157° C.-158° C.

All disclosure relevant to the preparation of 4-[α-(4-cyanophenyl)-1-(1,2,4-triazolyl)-methyl]benzonitrile described in Bowman, U.S. Pat. No. 4,749,713 is hereby incorporated by reference herein.

Example 2

Formulations of 4,4'-[fluoro-(1-H-1,2,4-triazol-1-yl)methylene]bisbenzonitrile (CGP47645)

4,4'-[Fluoro-(1-H-1,2,4-triazol-1-yl)methylene]bisbenzonitrile (CGP47645) is provided in the form of hard gelatine capsules representing an immediate release dosage form for oral administration. The dosage form is a hard gelatine capsule containing a white to yellowish powder in a pink opaque capsule, size 1 or 3. Three strengths are provided, containing 0.1 mg, 0.5 mg or 1.0 mg CGP47645 per hard gelatine capsule. The excipients used to prepare the hard gelatine capsules are lactose, microcrystalline cellulose, corn (maize) starch, sodium starch glycolate, magnesium stearate, colloidal silicon dioxide. All the excipients comply with the requirements of the applicable compendial monographs (Ph.Eur., NF). The hard gelatine capsules are packaged in HDPE bottles with aluminum induction seal equipped with child-resistant screw-cap closures.

CGP47645 containing hard gelatine capsules are prepared by the following process: The required excipients, in the respective amounts to yield the final composition as indicated in Table 2 below, and the appropriate amount of CGP47645 drug substance are weighed. Then, approximately 50% of corn starch is filled into suitable container, the drug substance is added, followed by the remaining 50% of corn starch to get a sandwich of drug substance between two layers of maize starch. Blending and sieving this mixture yields the drug substance (DS) premix. The remaining excipients (microcrystalline cellulose, spray-dried lactose, sodium starch glycolate, and colloidal silicon dioxide [Aerosil® 200]) are mixed and sieved and transfer into a suitable container. Then the DS premix is added into container containing the sieved excipients and the mixture is blended together. Finally, pre-sieved Magnesium stearate is added to the blend containing the DS and this mixture is blended again to yield the final blend. The final blend is filled into hard gelatin capsules.

The following Table 2 indicates the composition of the CGP47645 hard gelatin capsule of 0.1 mg, 0.5, 1 mg and 10 mg strength.

TABLE 2

| Ingredient | Amount per capsule (mg) | | | | |
| --- | --- | --- | --- | --- | --- |
| | 0.1 mg[1] | 0.1 mg[2] | 0.5 mg[1] | 1 mg[2] | 10 mg[2] |
| Capsule content | | | | | |
| CGP47645 | 0.1 | 0.1 | 0.5 | 1.0 | 10.0 |
| Lactose monohydrate | 96.0 | 192.0 | 96.0 | 192.0 | 175.5 |
| Cellulose, microcrystalline | 30.0 | 60.0 | 30.0 | 60.0 | 50.0 |
| Corn Starch | 14.15 | 28.4 | 13.75 | 27.5 | 40.0 |
| Sodium starch glycolate (Type A) | 7.5 | 15.0 | 7.5 | 15.0 | 15.0 |
| Magnesium Stearate | 1.5 | 3.0 | 1.5 | 3.0 | 3.0 |
| Silica, colloidal anhydrous | 0.75 | 1.5 | 0.75 | 1.5 | 1.5 |
| Capsule fill weight | 150.0 | 300.0 | 150 | 300.0 | 295.0 |
| Empty capsule shell | | | | | |
| Capsule shell | 48.0 | 76.0 | 48.0 | 76.0 | 76.0 |
| Total capsule weight | 198.0 | 376.0 | 198.0 | 376.0 | 371.0 |

[1]Filled in size 3 capsules;
[2]Filled in size 1 capsules

Example 3

Single ascending dose study of 4,4'-[Fluoro-(1-H-1,2,4-triazol-1-yl)methylene]bisbenzonitrile (CGP47645)

This was a randomized, double-blind, placebo- and active-controlled single ascending dose study in pre- and post-menopausal women to assess the safety and tolerability, PK and PD effects of single doses of 4,4'-[Fluoro-(1-H-1,2,4-triazol-1-yl)methylene]bisbenzonitrile (CGP47645). There were 8 cohorts of 8 post-menopausal subjects randomized 6:2, CGP47645:placebo, who received single doses of CGP47645 beginning at the dose of 0.01 mg and carried through 20 mg, which reached the limit of the toxicology exposure coverage. Patients received either 0.1 mg, 1 mg, and 10 mg drug substance containing hard gelatin capsules or appropriate matching placebo capsules. For the lowest two dosing cohorts, 0.1 mg drug containing capsules were used for reconstituting the CGP47645 oral solutions for dosing the 0.01 and 0.03 dosing strength (Cohort 1 and 2).

A minimal toxic dose (MTD) was not reached. A single cohort of 8 pre-menopausal subjects without childbearing potential (Cohort No. 9) received CGP47645 0.1 mg or placebo, randomized 6:2, and one last cohort received letrozole 2.5 mg as an internal positive control cohort for the PD measurements. Table 3 presents the PK parameters based on preliminary analysis of the concentration-time profile obtained from this study.

TABLE 3

CGP47645 Pharmacokinetics in Post- & Pre-menopausal women

| Dose (mg) | Cohort No. | Cohort Size | $C_{max}$ (ng/mL) Mean | $C_{max}$ (ng/mL) CV (%) | $T_{max}$ (hr) Median | AUC(0-$t_{last}$) (ng*hr/mL) Mean | AUC(0-$t_{last}$) (ng*hr/mL) CV (%) | $T_{1/2}$ (days) Mean | $T_{1/2}$ (days) CV (%) |
|---|---|---|---|---|---|---|---|---|---|
| 0.01 | 1 | (n = 5) | 0.2 | 21.7 | 1 | 1.4 | 53.2 | 2.3 | 127.5 |
| 0.03 | 2 | (n = 6) | 0.4 | 18.7 | 0.6 | 24.1 | 34.0 | 16.5 | 36.0 |
| 0.1 | 3 | (n = 6) | 1.8 | 13.4 | 1 | 123.1 | 10.7 | 18.2 | 10.9 |
| 0.3 | 4 | (n = 6) | 5.1 | 14.1 | 1 | 605.1 | 49.0 | 23.5 | 19.9 |
| 1 | 5 | (n = 5) | 12.8 | 22.0 | 1 | 3201.9 | 37.2 | 22.4 | 38.5 |
| 3 | 6 | (n = 6) | 38.4 | 17.0 | 1 | 10053.0 | 16.7 | 25.0 | 8.4 |
| 10 | 7 | (n = 6) | 123.8 | 26.4 | 2 | 41745.5 | 17.3 | 27.3 | 17.6 |
| 20 | 8 | (n = 6) | 269.8 | 30.9 | 2 | 76731.6 | 11.4 | 26.9 | 16.5 |
| 0.1 | 9 | (n = 6) | 1.7 | 15.1 | 1 | 116.2 | 17.1 | 23.5 | 31.0 |
| 2.5 | Letrozole | (n = 8) | 33.5 | 27.0 | 1 | 1667.7 | 40.8 | 2.9 | 40.7 |

CGP47645 exhibited dose proportional pharmacokinetics and a dose-dependent inhibition of estrone, estrone sulfate and estradiol. No differences in CGP47645 pharmacokinetics were observed between post- and pre-menopausal women. CGP47645 is rapidly absorbed with a $T_{max}$ of 0.5-2 hrs; the median $T_{max}$ occurred within 1 hour of ingestion. Both $C_{max}$ & AUC increased in a dose-proportional manner. CGP47645 exhibited low inter-subject variability of 10-30% and completely unexpected long half-life in the range of 23 to 27 days.

In postmenopausal women the study showed evidence of efficacy in PD parameters with estrone suppression at least equal to letrozole already at doses of 0.1 mg and 0.3 mg. In postmenopausal women, the lowest single dose at which transient estrogen suppression was seen was 0.01 mg; and the lowest single dose at which maximal estrogen suppression was observed in post-menopausal women, using chemiluminescence or radioimmunoassay, was 0.1 mg. No inhibition of other enzymes involved in steroid hormone synthesis or metabolism was observed; in particular there were no changes in androgen levels, progesterone, aldosterone, cortisol, ACTH, or 17-keto or 17-OH steroids in 24 hour urine collections. A final review of the individual listing for bone density and T-scores determined by DEXA indicated there were no notable changes in bone density over time for subjects in the CGP47645 cohorts that received a dose of 3 mg or less, or within the letrozole 2.5 mg cohort. For subjects in the 10 mg and 20 mg dose cohorts, there was a small but clinically significant decrease in bone density at the lumbar spine, but not at the hip, at 6 months compared to baseline.

Example 4

Pharmacokinetics of a single oral dose of 1 mg $^{14}$C-4,4'-[Fluoro-(1-H-1,2,4-triazol-1-yl)methylene]bis-benzonitrile in healthy postmenopausal women—ADME study The study was a single dose, single group, open label ADME study of 8 healthy postmenopausal women. Subjects enrolled in the study received 1 mg CGP47645 labeled with 10 μCi of 14C-CGP47645. The drug dose of 1 mg CGP47645 was selected as being presumably therapeutically relevant based on the animal ADME information and dosage information available for other aromatase inhibitors. The study design consisted of a 28-day screening period, one baseline visit (Day −1), a domiciled period beginning from admission on Day −1 through discharge on Day 7, 2 outpatient visits for PK blood collection on Days 14 (±1) and 21 (±1), 2 subject specific adipose tissue collection visits, and an end-of-study 6 month safety follow-up visit.

The primary goal of this study was to assess the partitioning of CGP47645 into abdominal adipose tissue as a measure of peripheral tissue targeting and to assess whether there may be a longer T½ metabolite, as well as to elucidate the metabolic profile, obtain information on routes of excretion and mass balance. Adipose tissue samples were collected in a sparse sampling protocol, where each subject underwent two collections of adipose tissue, with each subject biopsied at different times.

The single oral administration of 1 mg $^{14}$C-CGP47645 was found to be safe and well tolerated. Following single oral administration of 1 mg $^{14}$C-CGP47645 to healthy postmenopausal women, pharmacokinetics of CGP47645 can be characterized by fast and almost complete absorption followed by rapid decline in plasma concentrations suggesting extensive distribution into the tissues. This was followed by a prolonged terminal phase with low but persistent plasma concentrations lasting longer than 4000 hrs post-dose. The terminal elimination half-life was estimated to be approximately 28 days. Concentration time profiles suggest fast equilibration of CGP47645 between tissue and blood followed by slow elimination of CGP47645 from blood which is the rate limiting step for the CGP47645 clearance. This is reflected by parallel terminal slopes in plasma and adipose tissue, i.e. the elimination rates in plasma and tissue are similar.

Approximately 84% of the total radioactivity excreted after 6 days was renally eliminated of which only 16% was recovered as unchanged drug. No metabolites were detected in plasma and $^{14}$C-CGP47645 was the only radioactive compound detected in all analyzed plasma samples. Concentration-time profiles in plasma of $^{14}$C-CGP47645 measured by liquid scintillation counting [LSC] and parent CGP47645 measured by liquid chromatography-mass spectroscopy [LC-MS] were almost super imposable further suggesting absence of metabolite(s) in plasma. However, major mechanism of $^{14}$C-CGP47645 elimination appears to be metabolism followed by renal excretion. Three main metabolites identified in urine were a carbinol derivative and two glucuronides of CGP47645. Metabolite patterns were comparable for urine samples from different time points suggesting that formation of metabolites was the rate limiting step.

Overall, pharmacokinetics of $^{14}$C-CGP47645 can be characterized by fast absorption followed by rapid decline in plasma concentrations suggesting extensive distribution into the tissues. The terminal elimination half-life of the parent drug was estimated to be approximately 28 days.

Example 5

Study to analyse whether oral 4,4'-[Fluoro-(1-H-1,2,4-triazol-1-yl)methylene]bisbenzonitrile increases or normalizes testosterone levels in obese hypogonadotropic hypogonadal men This is an open-label dose finding study followed by a parallel group, randomized, double-blind study to evaluate the safety, tolerability and pharmacodynamics of 12 week treatment with 4,4'-[Fluoro-(1-H-1,2,4-triazol-1-yl)methylene]bisbenzonitrile (CGP47645) in obese, hypogonadotropic hypogonadal men. The study is designed as a 2-part study, with Part 1 being open-label to best determine the appropriate dose levels to use in Part 2, which has a randomized, double-blind, placebo controlled design. The study assesses the safety and tolerability of CGP47645, and determines whether a low dose of CGP47645 given at a weekly dosing interval normalizes testosterone levels and improves insulin sensitivity in obese, hypogonadotropic hypogonadal (OHH) men when compared with placebo.

Study Design: As set out above, this is a two-part study in obese, hypogonadotropic hypogonadal (OHH) men, wherein Part 1 is a single group, open label, non-randomized study establishing appropriate dosing. After all subjects have successfully completed 4 weeks of treatment, they continue for up to a total of 12 weeks of treatment. Then Part 2 follows as a parallel group, randomized, double-blind, placebo-controlled design, for 12 weeks of treatment, with an interim analysis after 4 weeks of treatment. Both Parts of the study have up to a 28 day screening period, a single baseline day, a 12 week treatment period (11 weekly doses), followed by a 3 month follow-up period.

The Screening Period is used to assess eligibility and to taper patients off disallowed medications. Subjects who meet the inclusion/exclusion criteria at Screening are admitted to Baseline evaluations. Subjects are admitted to the study site the night prior to Oral Glucose Tolerance Test (OGTT) evaluations to ensure fasting conditions are maintained. The same overnight domiciling applies for all scheduled OGTT evaluation days. Following the first dose, pharmacokinetic (PK), pharmacodynamic (PD), and safety assessments are collected for up to 24 hours. Subjects return to the site 1-2 days prior to each of the next 10 dosing visits for pharmacodynamic blood evaluations in Part 1, and up to 72 hours prior to each dosing visit in Part 2. At the conclusion of the 12 week treatment period, patients are asked to return to the site approximately once every 6 weeks for 3 months for safety follow-up evaluations. Safety assessments include physical examinations, ECGs, vital signs, standard clinical laboratory evaluations (hematology, blood chemistry and urinalysis), adverse event and serious adverse event monitoring. PK and PD (sex steroid) assessments take place on multiple occasions throughout the duration of the study, and are collected at the same time whenever both are scheduled on the same visit.

The 0.01 mg dose of CGP47645 administered once weekly was chosen as starting dose on the basis of the extremely long half-life of CGP47645 of approximately 22-29 days in serum and potentially even longer in adipose tissue, its linear PK profile, minimal inter patient variability. Pharmacokinetic modeling was used to define the impact of dose frequency and dose on steady state exposure. Once weekly dosing was selected as the optimal approach for initial evaluation. The model was used to estimate the dose of CGP47645 required to normalize testosterone in OHH men, and the potential impact of a loading dose. Pharmacodynamic predictions are also based on the minimal dose (0.01 mg) in women demonstrated to have pharmacodynamic effects in the single ascending dose study (Example 3).

Thus, for Part 1 of the study, it was decided to start with 0.01 mg as the loading dose, assess the testosterone response at 5 or 6 days after a single dose, and adjust the next weekly dose up or down based on the acute testosterone response. The weekly maintenance dose is not expected to exceed 0.5 mg. For at least the first 4 weeks of treatment, subject's sex steroid levels are measured prior to their subsequent dosing. The subsequent dose is the adjusted based on the prior response.

For Part 2, the blinded study, dose adjustment based on clinical discussions and/or an algorithm for both CGP47645 and placebo (based on findings in Part 1). A fixed dose regimen consisting of a starting dose of 0.3 mg followed by a 0.1 mg weekly dosing was selected for Part 2 of the study.

For Part 1, the dose range finding part of the trial, if testosterone levels are in the normal range, 1/5 of the loading dose of CGP47645 (0.002 mg) or placebo will be administered in Week 2. If free testosterone is above normal, the Week 2 dose will be 1/10 (0.001 mg) of the loading dose. If free testosterone is below normal, the Week 2 dose will be ½ of the loading dose (0.005 mg). Subsequent weekly doses are adjusted on a ½ log order to achieve normalization of free testosterone levels.

Study Drug:

1 mg (size 1) and 0.1 mg (size 3) capsules of CGP47645 for oral intake as depicted in Example 2; lower doses for this study will be diluted in solution.

Population:

A total of approximately 44 subjects will be randomized to participate in the study. The subjects are adult male patients meeting the criteria of obese, hypogonadotropic hypogonadism (OHH) who have passed screening assessments, comply with inclusion/exclusion criteria and have provided written consent. For Part 1, about 14 patients are required, whereas Part 2 required up to 30 patients, randomized to active and placebo treatment in a 1:1 ratio.

Inclusion Criteria Comprise:
1. Males who meet the criteria of obese, hypogonadotropic hypogonadism defined as:
   a. Patients with a Body Mass Index (BMI) ≥30 kg/m$^2$
   b. Patients with a morning serum total testosterone level <300 ng/dL on at least two separate occasions during the Screening and/or Baseline periods
   c. Patients with inappropriately low gonadotropins at screening given the low testosterone:
      i. Luteinizing hormone (LH) ≤ULN
      ii. Follicle stimulating hormone (FSH) ≤ULN
      iii. Estradiol within or above the normal range (defined as ≥LLN of the approved assay)
   d. Normal hypothalamic/pituitary function, including:
      i. Prolactin: within the normal range
      ii. Thyroid stimulating hormone (TSH): within the normal range
      iii. Ferritin: within the normal range
2. Patients agree to use a barrier method of contraception (e.g., condom), for the duration of the study and for at least 3 months following their Study Completion visit to prevent compound exposure to their partners.

Exclusion criteria comprise patients with hypogonadism, not related to obesity or as a result of other underlying issues; and patients with significant major organ class illness (e.g. kidney or liver disease).

The primary objective of this study is to demonstrate that weekly administration of low doses of CGP47645 normalize testosterone levels in obese, hypogonadotropic hypogonadal (OHH) men. Furthermore, the pharmacodynamic effect of CGP47645 on insulin sensitivity (based on HOMA-IR) in OHH men is to be demonstrated.

Secondary objectives of this study include the assessment of the safety and tolerability of CGP47645 in OHH men, assessment of the pharmacodynamic effect of CGP47645 on glucose, insulin and lipid metabolism, and body composition in OHH men, and the determination of the pharmacokinetics of CGP47645 in OHH men.

Assessments and Evaluations: The Following Assessments Will be Performed During the Study:

1. Background, demographic and administrative assessments
    Inclusion/exclusion criteria; Relevant medical history/ Current medical conditions
    Demography
    Physical examination, including digital prostate examination
    International Prostate Symptom Score (IPSS)
    Hepatitis screen, HIV screen
    Alcohol test, Drug screen
    Prolactin, ferritin and thyroid stimulating hormone (TSH)
    Drug administration: each time study drug is administered
    Study Completion information
    Comments
2. Safety and tolerability assessments
    Vital signs and body measurements
        Body height (BMI will be calculated)
        Body weight*
        Body temperature
        Blood pressure, pulse rate
    ECG evaluations
    Hematology; Blood chemistry; Urinalysis
    Prostate specific antigen (PSA)
    Adverse events: from time of first administration of study drug until Study Completion. Adverse events occurring before starting study treatment but after signing the informed consent form are recorded on the Medical History/Current Medical Conditions Case Report Form.
    Serious adverse events: from time of consent until 30 days after Study Completion
    Concomitant medications/Significant non-drug therapies: Refer to entry criteria and Concomitant medication for details of recording requirements for allowed and restricted medications during the study.
3. Pharmacokinetic (PK) blood assessments: PK samples will be collected on multiple occasions during the treatment phase of the study. PK assessments will also be collected every 6 weeks during the safety follow-up period. It is anticipated that the final PK draw will take place at Week 24/EOS, with the possibility of additional samples being collected if there is still clinically relevant detectable blood CGP47645 levels after that time.
4. Pharmacodynamic assessments (to be collected at the same time of day on each collection day)
    Sex hormones:
        Testosterone (total)
        Estradiol (total)
        Sex hormone binding globulin (SHBG)
        Bioavailable testosterone
        Dihydrotestosterone (DHT)
        Note: Free testosterone and free estradiol will be calculated from the total testosterone/estradiol and SHBG levels
    Luteinizing hormone (LH), follicle stimulating hormone (FSH) and inhibins A and B
    Semen analysis for sperm count and motility, only if study is open to non-vasectomized males
    Body composition (by DEXA)
    Body measurements
        Body weight (derived BMI)
        Waist circumference, hip circumference (derived waist-hip ratio)
    OGTT: Blood sampling at −10 minutes pre-glucose, 0 (pre-glucose), 15, 30, 60, 90, 120 and 180 minutes post-glucose load.
        Glucose
        Insulin
        HOMA-IR and QUICKI (derived from fasting insulin and glucose values)
        HbA1c (will be part of safety lab collection)
    Fasting lipid parameters (LDL, HDL, triglycerides)
    Bone biomarkers: C-terminal telopeptide (CTx1), osteocalcin, bone alkaline phosphatase and procollagen type 1 N-propeptide (PINP)
    Muscle function assessment by power stair climb
    Quality of life questionnaire: Aging Males' Symptom (AMS) Scale Analysis Methods—Efficacy and Pharmacodynamic Analyses:

Part 1 is designed as an open label dose finding phase. The primary efficacy endpoint at the end of Week 4 in Part 1 is the demonstration that total and free testosterone and estradiol can be normalized in the subjects who have received an appropriate dose.

The primary objective of Part 2 of the study is to assess the impact of normalizing testosterone with CGP47645 on insulin sensitivity. The data of the primary efficacy/pharmacodynamic variable, HOMA-IR, is transformed into log scale, for both baseline and on-treatment values, and analyzed using analysis of covariance at each time point with treatment as a classification variable and baseline as a covariate. Point estimates and 95% confidence intervals of the treatment differences are derived from the analysis of covariance. The related insulin sensitivity index, QUICKI, is analyzed similarly. The correlation between changes in testosterone level and changes in HOMA-IR values or in QUICKI values is assessed.

The secondary efficacy/pharmacodynamic variables, including sex hormone levels, fasting and postprandial glucose (AUC and peak), postprandial insulin, HbA1c, fasting lipids, body weight, waist-to-hip ratio, Luteinizing hormone (LH), follicle stimulating hormone (FSH), inhibin A and B, and muscle function assessment by stair climb power, is similarly analyzed. Log-transformation of the data may be performed as appropriate. For data distributions requiring a nonparametric approach for analysis, Wilcoxon rank sum test is used.

Data on bone biomarkers—C-terminal telopeptide (CTx1), osteocalcin, bone alkaline phosphatase and procollagen type 1 N-propeptide (PINP) as well as data on semen analysis and quality of life questionnaires are summarized by descriptive statistics.

Preliminary results of the initial 12 week treatment, open label dose-finding portion of the study: 14 obese, hypogonadal men received weekly oral doses of CGP47645 from 0.003 mg to 5 mg. For example, patients received weekly oral doses of 0.1 mg per dose; of 0.3 mg per dose; of between 0.01 mg and 0.03 mg per dose; of between 0.003 mg and 0.3 mg per dose; of between 0.003 mg and 1 mg per dose; of between 0.1 mg and 0.3 mg per dose; of between 0.01 mg and 1 mg per dose; of between 0.2 mg and 1 mg per dose; of between 0.3 mg and 1 mg per dose; of between 0.1 mg and 3 mg per dose; or of between 1 mg and 5 mg per dose. Doses were adjusted to normalize testosterone, and if cumulative exposures approached the highest single dose exposures tested (20 mg) in postmenopausal women then dosing was stopped during the 12 weeks. All subjects tolerated CGP47645 well without frequent AEs, no SAEs and no withdrawals. Preliminary analysis reveals that testosterone (measured by RIA) rose in all men individually into the normal range and on average into the normal range during treatment. Preliminary results indicate that the average change of testosterone from baseline to week 12 was approximately 2-fold (250±22.3 ng/dL to 550±191.8 ng/dL). Based on additional preliminary analysis serum estradiol (measured by LC-MS) was reduced by approximately 30-50% (average change from baseline to week 12 is 24±4.9 pg/mL to 18±9.4 pg/mL) but was not suppressed (lower limit of detection is 2 pg/mL) as assessed by highly sensitive LC-MS assays.

Cited and Further Related Literature

Barry M J, Fowler F J, O'leary M P et al (1992). The American Urological Association Symptom Index for benign prostatic hyperplasia. Journal of Urology, 148: 1549-1557

Bathnagar, et al (1996), Pharmacology of Nonsteroidal Aromatase Inhibitors, in "Hormone-dependent cancer" By Jorge R. Pasqualini, Benita S. Katzenellenbogen, Published by Informa Health Care, 1996, ISBN 0824796977, pp 155-168.

Batzl-Hartmann et al (1994) Pharmacological Profile of CGP47645, a new non-steroidal aromatase inhibitor with a long duration of action. In: Rao et al, eds. Proceedings of the XVI International Cancer Congress, Bologna: Monduzzi Editore, 1994: 3041-3047.

Bhasin S, Cunningham G R, Hayes F J, Matsumoto A M, Snyder P J, Swerdloff R S and Montori V M (2006). Testosterone Therapy in Adult Men with Androgen Deficiency Syndromes: An Endocrine Society Clinical Practice Guideline. The Journal of Clinical Endocrinology & Metabolism, 91:1995-2010 de Boer H, Verschoor L, Ruinemans-Koerts J and Jansen M (2005). Letrozole normalizes serum testosterone in severely obese men with hypogonadotropic hypogonadism. Diabetes, Obesity and Metabolism, 7: 211-215

EP 490 816 and U.S. Pat. No. 5,637,605

Hofstra J, Loves S, van Wageningen B, Ruinemans-Koerts J, Janssen H and de Boer H (2008). High prevalence of hypogonadotropic hypogonadism in men referred for obesity treatment. Netherlands journal of medicine, 66: 103-109

Kapoor D, Aldred H, Clark S, Channer K S and Jones T H (2007). Clinical and Biochemical Assessment of Hypogonadism in Men With Type 2 Diabetes. Diabetes Care, 30: 911-917

Kapoor D, Goodwin E, Channer K S, Jones T H (2006). Testosterone replacement therapy improves insulin resistance, glycaemic control, visceral adiposity and hypercholesterolaemia in hypogonadal men with type 2 diabetes. Eur J Endocrinol. 2006 June; 154(6):899-906

Lapauw B, T'Sjoen G, Mahmoud A, Kaufman J M and Ruige J B (2009). Short-term aromatase inhibition: effects on glucose metabolism and serum leptin levels in young and elderly men. European Journal of Endocrinology, 160: 397-402

Loves S, Ruinemans-Koerts J and de Boer H (2008). Letrozole once a week normalizes serum testosterone in obesity-related male hypogonadism. European Journal of Endocrinology, 158: 741-747

Maggio M, Basaria S (2009). Welcoming low testosterone as a cardiovascular risk factor. International Journal of Impotence Research 21: 261-264

Medras M, Jozkov Pawel and Slowinska-Lisowska M (2007). Serum, Seminal Plasma, and Sperm Count Monitoring During Treatment of Idiopathic Gynecomastia With an Aromatase Inhibitor. The Endocrinologist, 17: 302-305

Naharci M I, Pinar M, Bolu E and Olgun A (2007). Effect of testosterone on insulin sensitivity in men with idiopathic hypogonadotropic hypogonadism. Endocrine Practice, 13: 629-635

Trunet P F, Mueller P H, Bhatnagar A S, Dickes I, Monnet G and White G (1993). Open Dose-Finding Study of a New Potent and Selective Nonsteroidal Aromatase Inhibitor, CGS 20 267, in Healthy Male Subjects. The Journal of Clinical Endocrinology & Metabolism, 77: 319-232

The various features and embodiments of the present invention, referred to in individual sections above apply, as appropriate, to other sections, mutatis mutandis. Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for the treatment of hypogonadotropic hypogonadism in an overweight or obese male patient with serum total testosterone levels below 400 ng/dl and in need of increased testosterone levels comprising administering to said patient an effective amount of the compound 4,4'-[fluoro-(1-H-1,2,4-triazol-1-yl)methylene]bisbenzonitrile, wherein the effective amount of the compound is from about 0.01 mg to about 1.0 mg per dose, and wherein the compound is administered according to a dosing regimen having a dosing periodicity selected from about one dose once weekly to about one dose once every month.

2. The method of claim 1, wherein the method is for the treatment of hypogonadotropic hypogonadism in an obese male patient.

3. The method of claim 1, wherein the testosterone level is increased by at least 10% in comparison to the testosterone level prior to administration of the compound.

4. The method of claim 1, wherein the testosterone level is normalized.

5. The method of claim 1, wherein the patient is in need of the prevention or treatment of one or more disorders selected from metabolic syndrome, type II diabetes, obesity, cardiovascular disease, insulin resistance, glucose intolerance and dyslipidaemia.

6. The method of claim 1, wherein the patient is in need of one or more of improved insulin sensitivity, improved glucose metabolism and an improved lipid profile.

7. The method of claim 1, wherein the patient is in need of the prevention or treatment of one or more disorders selected from the group consisting of decreased libido, decreased spontaneous erections, erectile dysfunction, decreased fertility, loss of body hair, reduced shaving, lack of energy, fatigue, impaired cognition, depression, changes in mood, low bone mineral density, increased risk of fractures, decreased muscle mass, decreased muscle strength, increased abdominal fat mass and limited body performance capacity.

8. The method of claim 1, wherein the patient is in need of one or more of increased muscle mass and strength, a normalized body composition, a decrease in abdominal fat mass, an improved sexual function and desire, increased fertility and increased bone mineral density.

9. The method of claim 1, wherein the effective amount of 4,4'-[fluoro-(1-H-1,2,4-triazol-1-yl)methylene]bisbenzonitrile further comprising the administration of a loading dose of 0.3 mg.

10. The method according to claim 1 or 9, wherein the effective amount of 4,4'-[fluoro-(1-H-1,2,4-triazol-1-yl)methylene]bisbenzonitrile is about 0.1 mg per dose administered about once weekly.

11. The method of claim 10, wherein said patient is an obese male and said testosterone is normalized.

12. The method of claim 1, wherein the effective amount of 4,4'-[fluoro-(1-H-1,2,4-triazol-1-yl)methylene]bisbenzonitrile is orally administered to the patient.

13. The method of claim 1, wherein 4,4'-[fluoro-(1-H-1,2,4-triazol-1-yl)methylene]bisbenzonitrile is administered according to a dosing regimen having a dosing periodicity selected from about one dose once weekly, about one dose once every 10 days, about one dose once biweekly, about one dose once every 3 weeks, about one dose once every 4 weeks, and about one dose once monthly.

14. The method of claim 13, wherein 4,4'-[fluoro-(1-H-1,2,4-triazol-1-yl)methylene]bisbenzonitrile is administered according to a dosing regimen having a dosing periodicity of about one dose once biweekly.

15. The method of claim 13, wherein 4,4'-[fluoro-(1-H-1,2,4-triazol-1-yl)methylene]bisbenzonitrile is administered according to a dosing regimen having a dosing periodicity of about one dose once monthly.

16. The method of claim 1, wherein 4,4'-[fluoro-(1-H-1,2,4-triazol-1-y1)methylene]bisbenzonitrile, when administered to the patient, shows an apparent elimination half-life chosen from one or more of at least about 14 days, at least about 20 days, at least about 25 days and at least about 30 days.

17. The method of claim 1, wherein when administering a single dose of 4,4'-[fluoro-(1-H-1,2,4-triazol-1-yl)methylene]bisbenzonitrile, said dose results in an increased effective blood concentration of testosterone over a period of time from 3 to 30 days.

18. The method of claim 17, wherein the serum concentration of testosterone is increased by at least 10% over the serum testosterone concentration prior to administration of the compound.

19. The method of claim 18, wherein serum estradiol is reduced by at least about 30%.

20. The method of claim 19, wherein the serum estradiol is reduced by about 30-50%.

21. The method of claim 20, wherein the serum estradiol is not suppressed.

* * * * *

UNITED STATES PATENT AND TRADEMARK OFFICE
CERTIFICATE OF CORRECTION

| | | |
|---|---|---|
| PATENT NO. | : 9,295,668 B2 | Page 1 of 1 |
| APPLICATION NO. | : 14/342810 | |
| DATED | : March 29, 2016 | |
| INVENTOR(S) | : Ann Taylor and Lloyd B. Klickstein | |

It is certified that error appears in the above-identified patent and that said Letters Patent is hereby corrected as shown below:

On the title page of the patent on Page 1, where the Assignee's name is listed, the spelling of the first word of the Assignee's name reading "Merco" should read --Mereo--.

Signed and Sealed this
Twenty-fourth Day of May, 2016

Michelle K. Lee
*Director of the United States Patent and Trademark Office*